US009402377B2

(12) United States Patent
Flavell et al.

(10) Patent No.: US 9,402,377 B2
(45) Date of Patent: Aug. 2, 2016

(54) HUMAN SIRPAALPHA TRANSGENIC ANIMALS AND THEIR METHODS OF USE

(75) Inventors: Richard A. Flavell, Guilford, CT (US); Till Strowig, New Haven, CT (US); Elizabeth Eynon, New Haven, CT (US); William Philbrick, New Haven, CT (US); Markus Manz, Zollikon (CH)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 13/847,636

(22) PCT Filed: Sep. 20, 2011

(86) PCT No.: PCT/US2011/052363
§ 371 (c)(1),
(2), (4) Date: Sep. 3, 2013

(87) PCT Pub. No.: WO2012/040207
PCT Pub. Date: Mar. 29, 2012

(65) Prior Publication Data
US 2013/0340105 A1    Dec. 19, 2013

Related U.S. Application Data

(60) Provisional application No. 61/403,694, filed on Sep. 20, 2010.

(51) Int. Cl.
*A01K 67/00* (2006.01)
*A01K 67/027* (2006.01)
*C07K 16/00* (2006.01)

(52) U.S. Cl.
CPC ............. *A01K 67/0278* (2013.01); *C07K 16/00* (2013.01); *A01K 2207/12* (2013.01); *A01K 2217/072* (2013.01); *A01K 2227/105* (2013.01); *A01K 2267/0381* (2013.01); *C07K 2317/14* (2013.01)

(58) Field of Classification Search
USPC .................................................. 800/8, 18, 3
See application file for complete search history.

(56) References Cited

U.S. PATENT DOCUMENTS 7,968,762 B2 * 6/2011 Vande Woude et al. ........ 800/18
8,541,646 B2 * 9/2013 Stevens et al. ................. 800/18
2008/0051556 A1 * 2/2008 Ullrich et al. ................. 530/300

FOREIGN PATENT DOCUMENTS

WO    WO 2008/010100    1/2008

OTHER PUBLICATIONS

Weijer (Blood, Apr. 15, 2002, vol. 99, p. 2752-2759).*
van Lent (J. Immunol., Nov. 2009, vol. 183, p. 7645-7655).*
Takenaka (Nature Immunol., Dec. 2007, vol. 8, No. 12, p. 1313-1323).*
Strowig (PNAS, Aug. 9, 2011, vol. 108, No. 32, p. 13218-13223).*
Cowan (Xenotransplantation, 2003, vol. 10, p. 223-231).*
Wall (1996, Theriogenology, vol. 45, p. 57-68).*
Ebert (1988, Mol. Endocrinology, vol. 2, pp. 277-283).*
Mullins (1990, Nature, vol. 344, p. 541-544).*
Hammer (1990, Cell, vol. 63, p. 1099-1112).*
Mullins, 1989, EMBO, vol. 8, p. 4065-4072.*
Taurog, 1988, J. Immunol., vol. 141, p. 4020-4023.*
Rongvaux (PNAS, early edition, Jan. 2011, p. 1-6).*
Rongvaux (PNAS, Feb. 8, 2011, vol. 108, No. 6, p. 2378-2383).*
Takenaka (Nature Immunol., Dec. 2007, vol. 8, No. 12, p. 1313-1323, Supplemental Material).*
Strowig (PNAS, 2011, 108, 13218-13223).*
Legrand et al., "Humanized Mice for Modeling Human Infectious Disease: Challenges, Progress, and Outlook," Cell Host Microbe, Jul. 2009, 6:5-9.
Manz, "Human-Hemato-Lymphoid-System Mice: Opportunities and Challenges, Immunity," May 2007, 26:537-541.
Ito et al., "NOD/SCID/gammac null mouse: an excellent recipient mouse model for engraftment of human cells," Blood, Nov. 2002, 100:3175-3182.
Ishikawa et al., "Development of functional human blood and immune systems in NOD/SCID/IL2 receptor gammachain null mice," Blood, Sep. 2005, 106:1565-1573.
Shultz et al., "Human Lymphoid and Myeloid Cell Development in NOD/LtSz-scid IL2R null Mice Engrafted with Mobilized Human Hemopoietic Stem Cells," J Immunol, Feb. 2005, 174:6477-6489.
Brehm et al., "Parameters for Establishing Humanized Mouse Models to Study Human Immunity: Analysis of Human Hematopoietic Stem Cell Engraftment in Three Immunodeficient Strains of Mice Bearing the IL2rγnull Mutation," Clin Immunol, Apr. 2010, 135:84-98.
Matozaki et al., "Functions and molecular mechanisms of the CD47—SIRPa signalling pathway," Trends Cell Biol, Jan. 2009, 19:72-80.
Okazawa et al., "Negative Regulation of Phagocytosis in Macrophages by the CD47-SHPS-1 System," J Immunol, Nov. 2004, 174:2004-2011.
2007, Wanatabe et al., "Humanized NOD/SCID/IL2R] null Mice Transplanted with Hematopoietic Stem Cells under Nonmyeloablative Conditions Show Prolonged Life Spans and Allow Detailed Analysis of Human Immunodeficiency Virus Type 1 Pathogenesis," J Virol, Dec. 2007, 81:13259-64.
2007, Takizawa and Manz, "Macrophage tolerance: CD47-SIRP-a-mediated signals matter," Nat Immunol, Dec. 2007, 8:1287-1289.
2007, Takenaka et al., "Polymorphism in Sirpa modulates engraftment of human hematopoietic stem cells," Nat Immunol, Dec. 2007, 8:1313-1323.

(Continued)

*Primary Examiner* — Michael Wilson
(74) *Attorney, Agent, or Firm* — Riverside Law LLP

(57) ABSTRACT

The invention relates generally to compositions and methods of using transgenic non-human animals expressing human SIRPα that are engrafted with a human hematopoietic system. In various embodiments, the human hematopoietic system engrafted, human SIRPα transgenic non-human animals of the invention are useful as systems for the in vivo evaluation of the growth and differentiation of hematopoietic and immune cells, for the in vivo assessment of an immune response, for the in vivo evaluation of vaccines and vaccination regimens, for in vivo production and collection of immune mediators, including human antibodies, and for use in testing the effect of agents that modulate hematopoietic and immune cell function.

10 Claims, 14 Drawing Sheets

(56) References Cited

OTHER PUBLICATIONS

Van Lent et al., "IL-7 enhances thymic T cell development in "human immune system" Rag2-/-IL-2Rgammac-/- mice without affecting peripheral T cell homeostasis," J. Immunol., Dec. 2009, 183(12):7645-55.

Shultz et al., "Humanized mice in translational biomedical research," J Immunol, Feb. 2007, 7:118-120.

Barclay et al., "Signal regulatory protein alpha (SIRPalpha)/CD47 interaction and function," Curr Opin Immunol, Feb. 2009, 21:47-52.

Koo et al., "Use of humanized severe combined immunodeficient mice for human vaccine development," Expert Rev Vaccines, Jan. 2009, 8:113-120.

Willinger et al., "Improving human hemato-lymphoid-system mice by cytokine knock-in gene replacement," Trends Immunol, Jul. 2011, 32:321-327.

\* cited by examiner

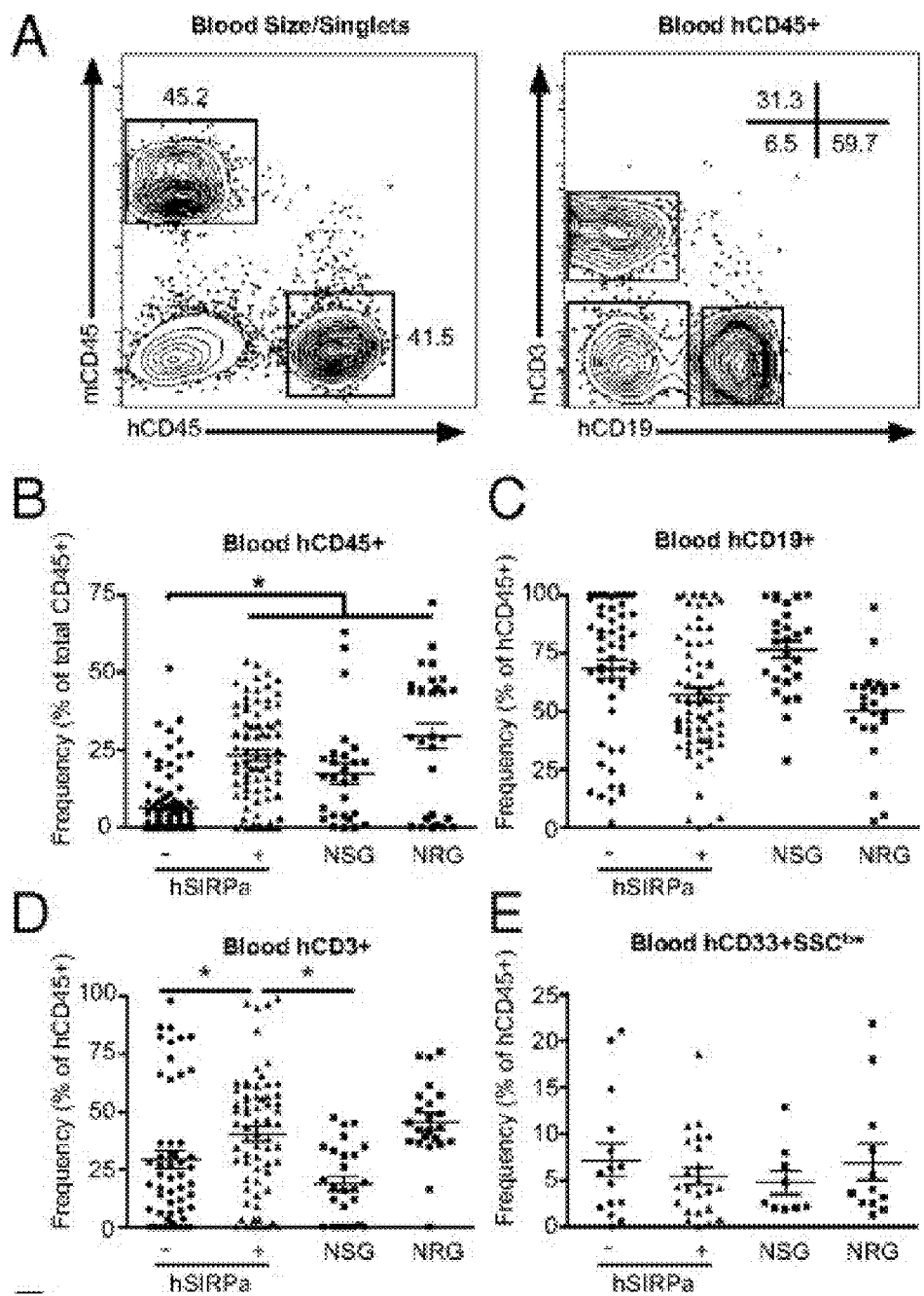
FIGURE 2 A-E

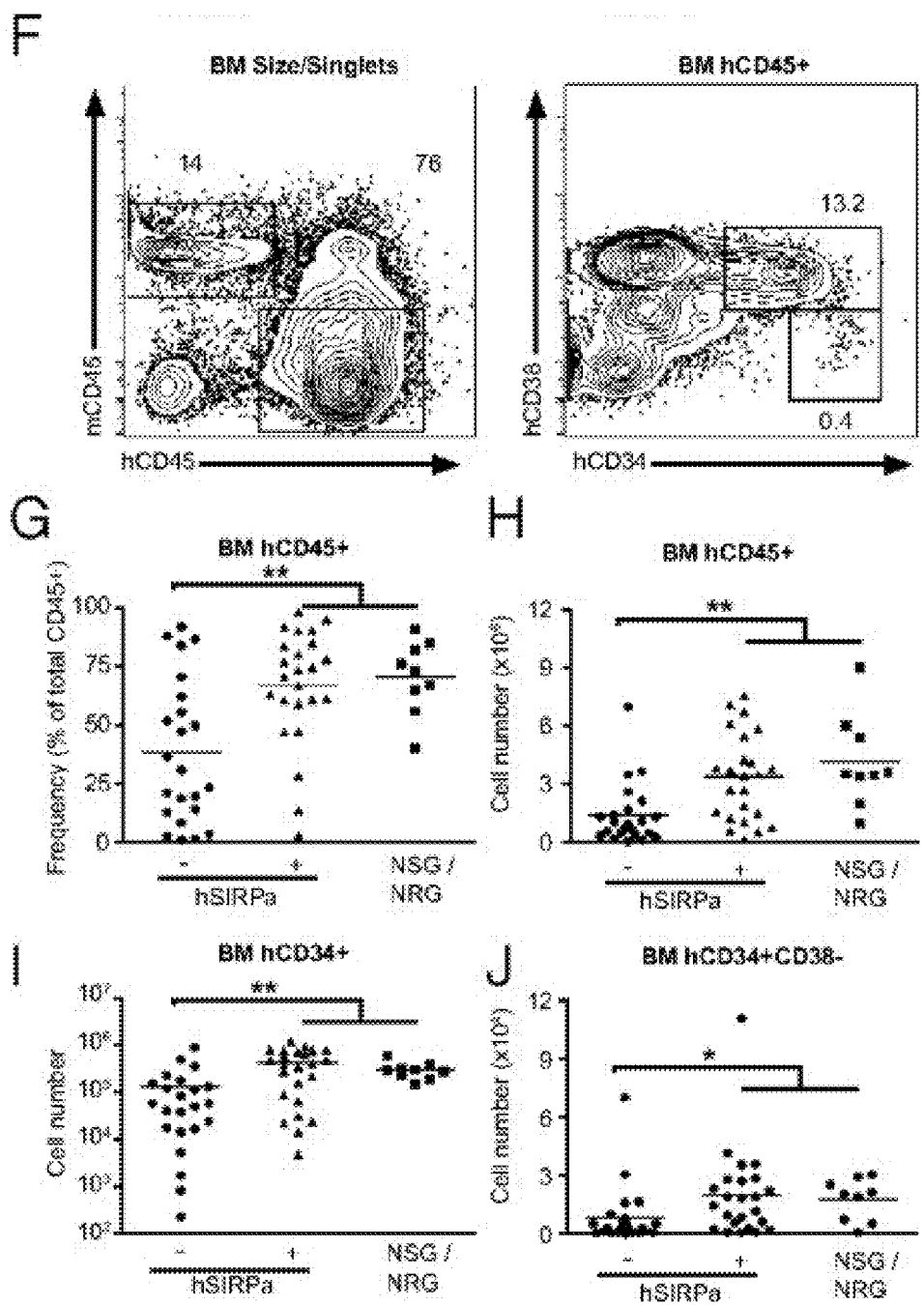
FIGURE 2 F-J

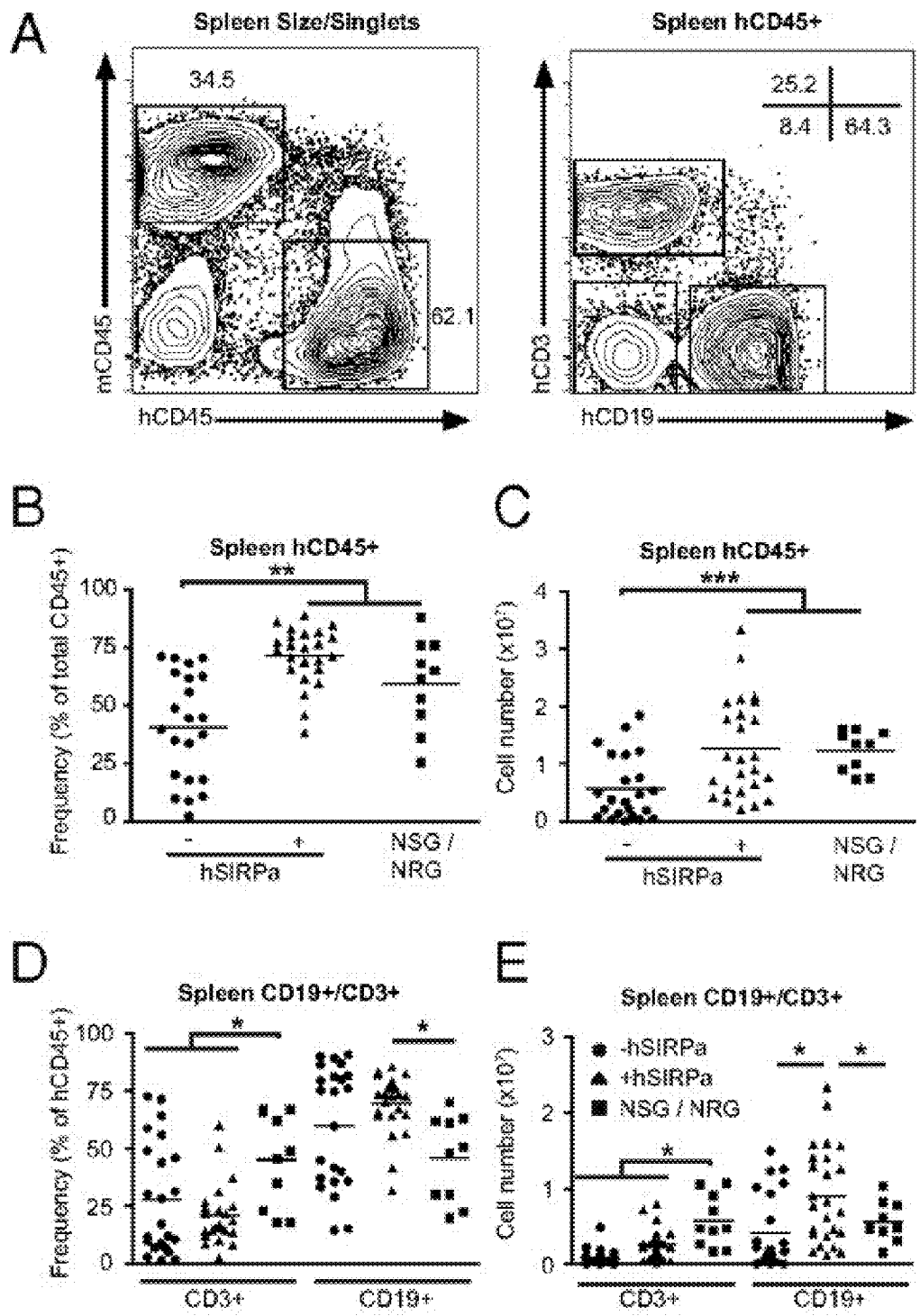
FIGURE 3 A-E

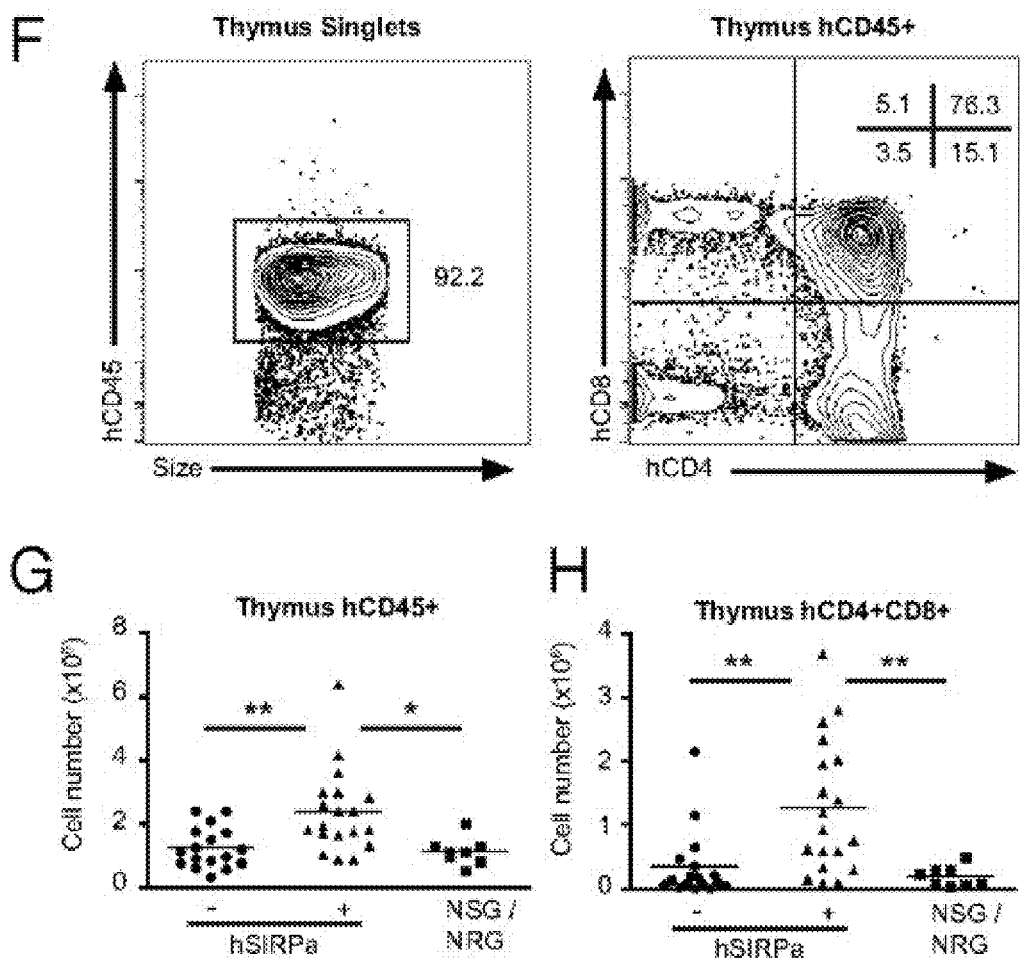
FIGURE 3 F-H

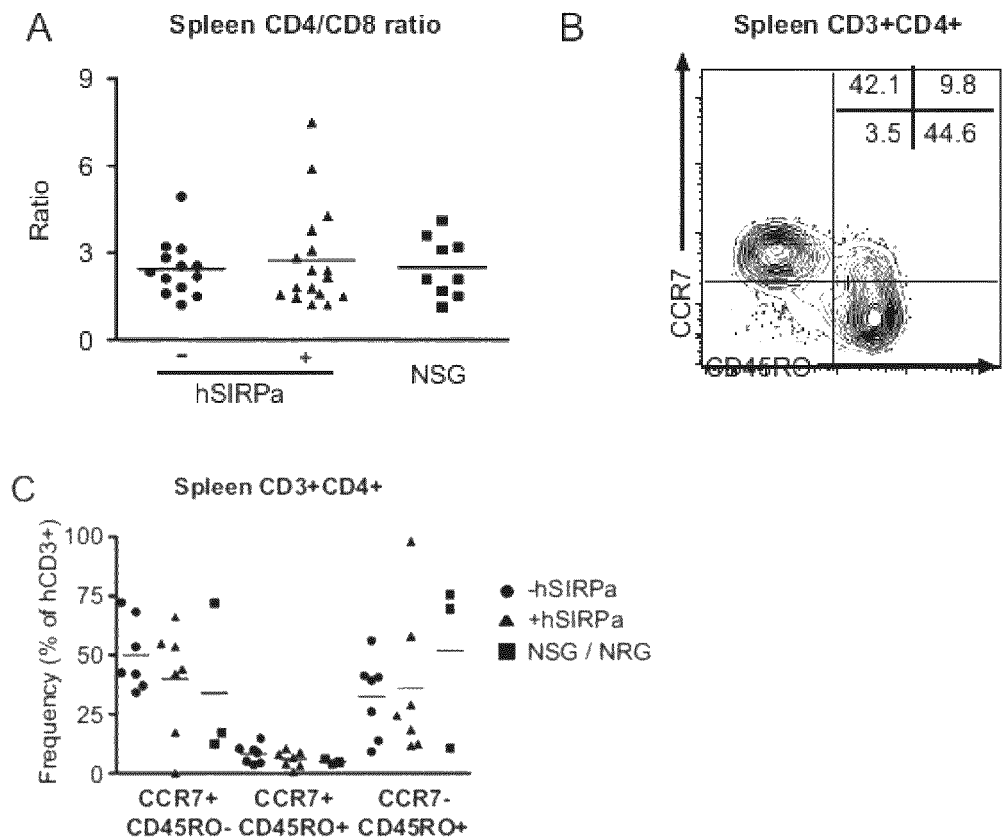
FIGURE 7 A-C

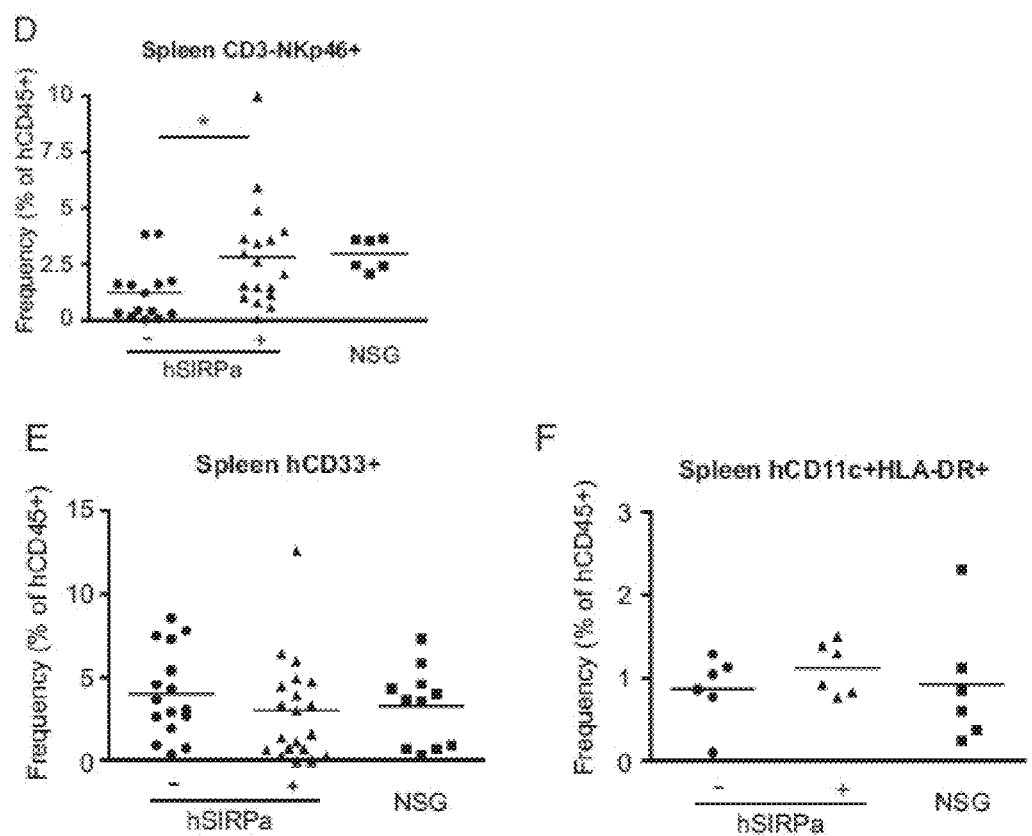
FIGURE 7 D-E

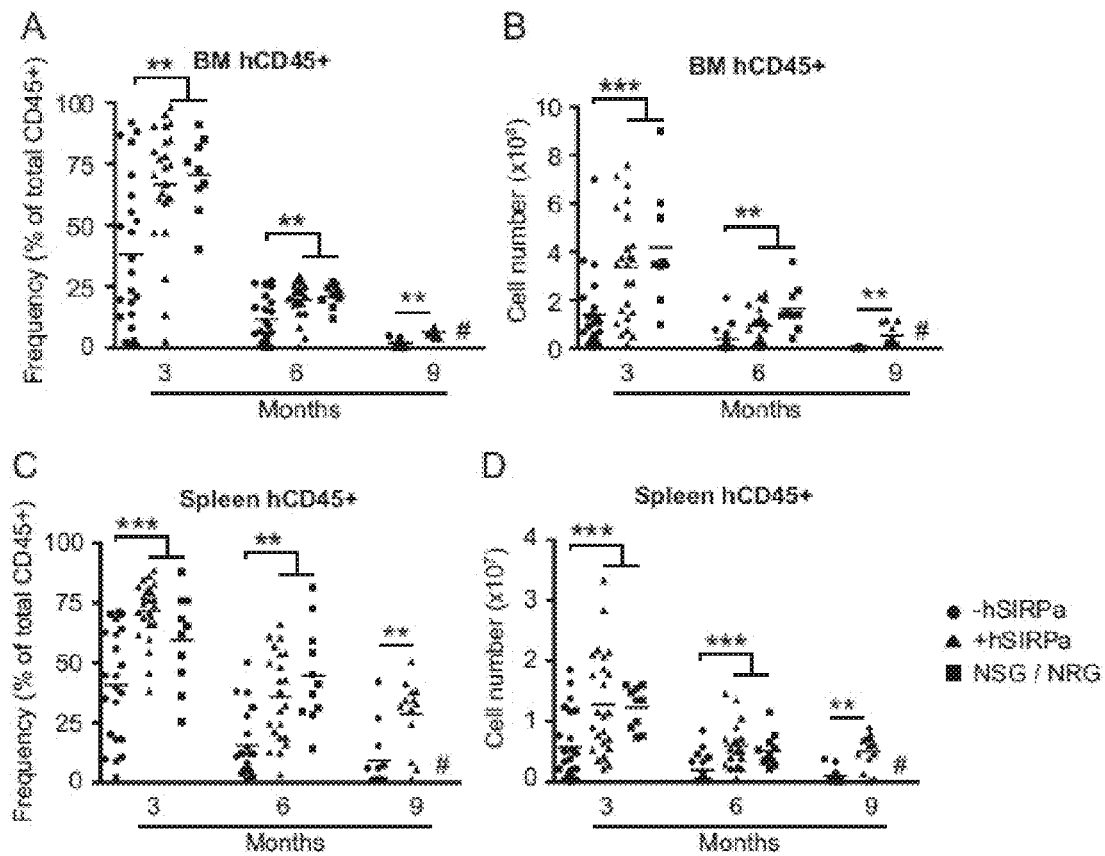
FIGURE 8 A-D

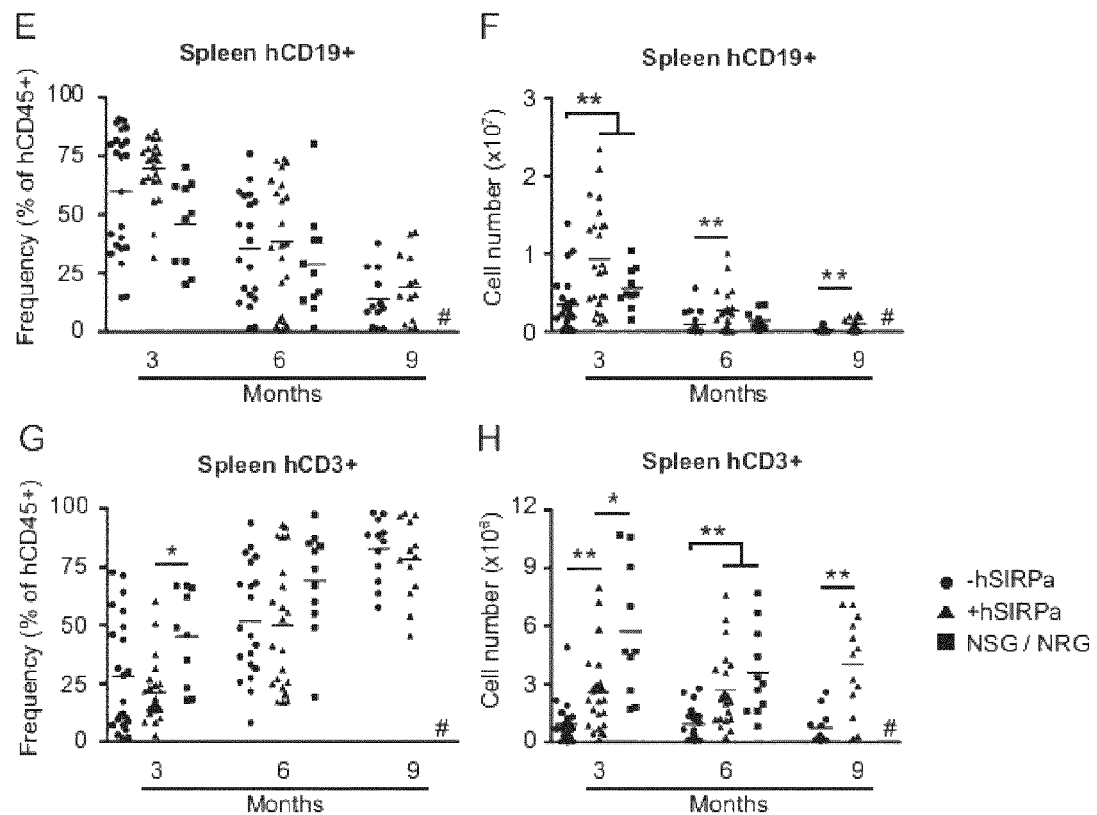
FIGURE 8 E-H

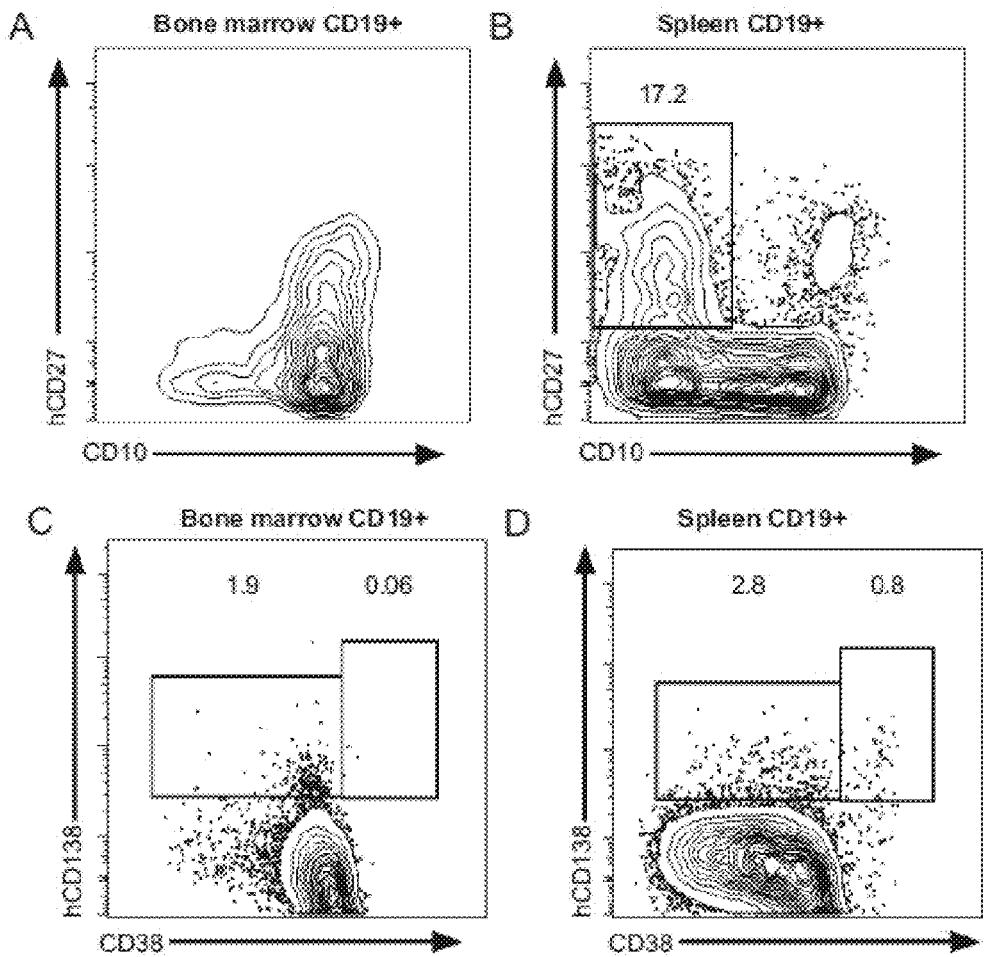
FIGURE 9 A-D

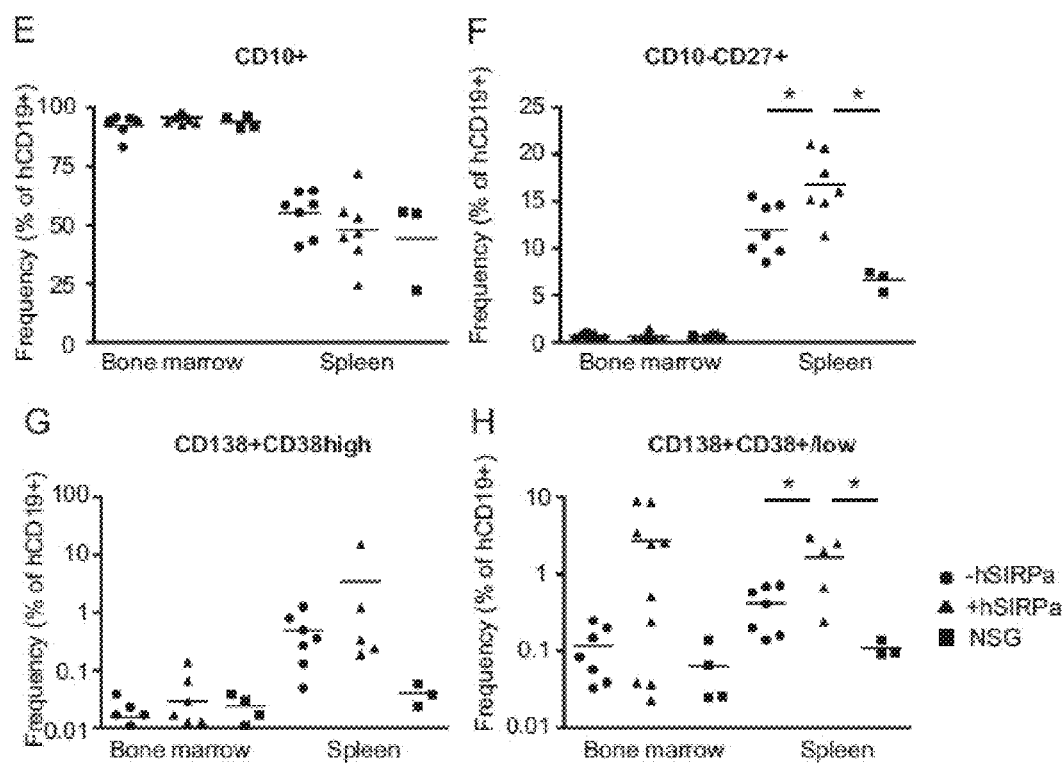
FIGURE 9 E-H

HUMAN SIRPAALPHA TRANSGENIC ANIMALS AND THEIR METHODS OF USE

CROSS-REFERENCE TO RELATED APPLICATION

The present application is a 35 U.S.C. §371 national phase application from, and claiming priority to, International Application No. PCT/US2011/052363, filed Sep. 20, 2011, and published under PCT Article 21(2) in English, which claims priority to U.S. Provisional Patent Application No. 61/403,694, filed Sep. 20, 2010, which applications are incorporated by reference herein in their entireties.

BACKGROUND OF THE INVENTION

Mice play a crucial role as the prime model organism to study many aspects of development and function in hematology and immunology. However, their habitats and pathogens that shape and constantly challenge the immune system have diverged between species, resulting in the fact that genes related to immunity, together with genes involved in reproduction and olfaction, are the most divergent between the two species (2004, Mestas and Hughes, J Immunol 172:2731-2738). Mice rendered genetically suitable to support human cells and tissues have become a favorite model bridging the gap between mouse models and studies in humans (2009, Legrand et al., Cell Host Microbe 6:5-9; 2007, Shultz et al., Nat Rev Immunol 7:118-130; 2007, Manz, Immunity 26:537-541). Particularly, mice that reconstitute a functional human immune system after engraftment of hematopoietic stem and progenitor cells (HSPCs) are of high interest to study vaccine candidates and the biology of pathogens restricted to humans in vivo. To achieve efficient xenotransplantation, mice lacking an adaptive immune system and natural killer (NK) cells have been successfully developed in the last years and the major models differ mainly in the background strains used. The first one employs the BALB/c Rag2$^{-/-}$γc$^{-/-}$ (DKO) mice, and neonatal intrahepatic HSPC transfer (2004, Traggiai et al., Science 304:104-107; 2004, Gimeno et al., Blood 104:3886-3893). A second model reconstitutes instead NOD/scid/γc−/− (NSG) mice by i.v. or intrahepatic injection of human HSPCs (2002, Ito et al., Blood 100:3175-3182; 2005, Ishikawa et al., Blood 106:1565-1573; 2005, Shultz et al., J Immunol 174:6477-6489). After transfer into these mice, human HSPCs can develop into most of the hematopoietic lineages and the human chimerism is maintained for several months (2004, Traggiai et al., Science 304:104-107; 2005, Ishikawa et al., Blood 106:1565-1573). Overall the composition of engrafted cells is similar in these models but higher human engraftment levels were obtained in NOD-based models (2010, Brehm et al., Clin Immunol 135:84-98). This advantage is thought to be caused at least partially by a polymorphism in the gene encoding the inhibitory receptor signal regulatory protein alpha (SIRPα) (2007, Takenaka et al., Nat Immunol 8:1313-1323).

SIRPα is a transmembrane protein containing three Ig-like domains in its extracellular region and putative tyrosine phosphorylation sites in its cytoplasmic region (2009, Matozaki et al., Trends Cell Biol 19:72-80). SIRPα is strongly expressed in neurons and in macrophages, dendritic cells, and neutrophils. The ligands of SIRPα are CD47 and surfactant A and surfactant D and their binding to the receptor induces the recruitment of phosphatases SHP-1 and SHP-2 to the plasma membrane. In phagocytic cells, this recruitment negatively regulates phagocytosis upon binding to its ligands (2005, Okazawa et al., J Immunol 174:2004-2011). CD47 is ubiquitously expressed in all cells of the body, including all lineages of hematopoietic cells. The inhibitory signaling via CD47-SIRPα ligation has important consequences in vivo because upon transfer into WT mice, CD47−/− cells are rapidly cleared by splenic red pulp macrophages (2000, Oldenborg et al., Science 288:2051-2054). Subsequently it was recognized that the regulation of CD47 expression plays important functions in such diverse biological processes as cell migration, the regulation of the erythrocyte life span, and HSC circulation (2000, Oldenborg et al., Science 288:2051-2054; 2009, Jaiswal et al., Cell 138:271-285; 2003, Motegi et al., EMBO J 22:2634-2644). Whereas it had been recognized that mouse phagocytes regulate human cell and tissue transplantation into mice (2004, Rozemuller et al., Exp Hematol 32:1118-1125; 1997, Terpstra et al., Leukemia 11:1049-1054; 2005, Andres et al., Transplantation 79:543-549), it has been recently demonstrated that, due to allelic variation, partial engagement of NOD SIRPα but not C57BL6 SIRPα on respective phagocytes by human CD47 leads to decreased phagocytosis of human cells in vitro (2007, Takenaka et al., Nat Immunol 8:1313-1323; 2007, Takizawa and Manz, Nat Immunol 8:1287-1289). Given the above discussed additional residual human engraftment impairment, it was hypothesized that expression of human SIRPα (i.e., hSIRPα or huSIRPα) on mouse macrophages would lead to decreased phagocytosis of human CD47-expressing cells (2000, Oldenborg et al., Science 288:2051-2054; 2001, Blazar et al., J Exp Med 194:541-549; 2007, Wang et al., Blood 109:836-842). Thus, to create an improved platform for future generations of humanized mice, human SIRPα transgenic mice were generated that faithfully express the receptor using F1 129/BALB/c Rag2$^{+/-}$γc$^{y/-}$ ES cells, which allow straightforward and rapid genetic modifications.

Severely immunocompromised mice lacking T cells, B cells, and NK cells have become widely used hosts for the xenotransplantation of human cells due to their diminished rejection of cells and tissues of human origin (2004, Traggiai et al., Science 304:104-107; 2002, Ito et al., Blood 100:3175-3182; 2005, Ishikawa et al., Blood 106:1565-1573; 2005, Shultz et al., J Immunol 174:6477-6489). However, it has been noted that there are additional strain-specific factors that influence engraftment efficiencies as demonstrated by the incapability of C57Bl6 Rag2$^{-/-}$γc$^{-/-}$, in contrast to NOD/Rag1$^{-/-}$γc$^{-/-}$ mice, to support engraftment of human cells. The importance of murine macrophages in xenorejection had been noted more than 10 y ago, but the mechanisms of xenorecognition were only described recently (2007, Takenaka et al., Nat Immunol 8:1313-1323; 2004, Rozemuller et al., Exp Hematol 32:1118-1125; 1997, Terpstra et al., Leukemia 11:1049-1054). It has been established that binding of CD47 on target cells to SIRPα on macrophages sends a "don't eat me" signal to the phagocyte, i.e., murine CD47$^{-/-}$ are rapidly cleared from WT mice (2000, Oldenborg et al., Science 288:2051-2054). In the context of xenotransplantation, the advantage of NOD/scid mice as hosts for human cells compared with CB17/scid or C57Bl6/Rag mice was subsequently suggested to require a specific variant of the polymorphic inhibitory receptor SIRPα (2007, Takenaka et al., Nat Immunol 8:1313-1323). A number of polymorphisms in the extracellular domain of SIRPα enabled SIRPα (NOD) to bind to human CD47, whereas SIRPα (C57B16) was unable to bind human CD47 (2007, Takenaka et al., Nat Immunol 8:1313-1323). In vitro assays were further used to characterize the direct effect of SIRPα on human hematopoiesis, but it remained formally unconfirmed whether SIRPα is sufficient for the enhanced engraftment in NOD-based strains. Notably, the NOD strain is characterized by a number of well-documented alterations in immune functions such as complement deficiency and impaired dendritic cell maturation (1995, Shultz et al., J Immunol 154:180-191).

Recently, several approaches have been used to improve human cell engraftment and the unbalanced lineage differentiation in CD34+ cell engrafted mice. These include transient approaches such as hydrodynamic injection of plasmid DNA (2009, Chen et al., Proc Natl Acad Sci USA 106:21783-21788), injections of cytokines, and infections of mice or CD34+ cells with lentiviruses (2010, O'Connell et al., PLoS ONE 5:e12009; 2009, Huntington et al., J Exp Med 206:25-34; 2009, van Lent et al., J Immunol 183:7645-7655). Alternatively, transgenic expression of human MHC molecules has been demonstrated to improve the development of antigen-specific immune responses in vivo (2009, Jaiswal et al., PLoS ONE 4:e7251; 2009, Strowig et al., J Exp Med 206: 1423-1434; 2011, Danner et al., PLoS ONE 6:e19826). Nonetheless, overexpression of cytokines might also have detrimental side effects due to the unphysiological expression such as in mice transgenic for GM-CSF, and IL-3 (2004, Nicolini et al., Leukemia 18:341-347). An alternative approach to provide human growth factors in vivo is to genetically engineer mice and replace the mouse genes with their human counterparts resulting in their expression in the appropriate niche at physiological levels. Indeed, faithful replacement of mouse GM-CSF and IL-3 as well as thrombopoietin (TPO) group has resulted in improved development of human macrophages in the lung and HSPC and HPC maintenance in the bone marrow, respectively (2011, Rongvaux et al., Proc Natl Acad Sci USA 94:5320-5325; 2011, Willinger et al., Proc Natl Acad Sci USA 108:2390-2395). Notably, in human TPO knockin mice, despite a highly increased engraftment level of stem and progenitor cells in the bone marrow, no changes were observed in the periphery, demonstrating the existence of limiting factors in the periphery such as destruction by phagocytes.

One application of mice with functional human immune systems is the development and testing of human vaccines. Historically, the induction of immune responses in vivo has been relatively inefficient (2004, Traggiai et al., Science 304: 104-107; 2002, Ito et al., Blood 100:3175-3182; 2005, Ishikawa et al., Blood 106:1565-1573; 2005, Shultz et al., J Immunol 174:6477-6489; 2006, Baenziger et al., Proc Natl Acad Sci USA 103:15951-15956). Several studies have reported successful pathogen-specific immune responses upon infection. Although it was reported that around 50% of mice produced virus-specific IgM and IgG upon dengue virus infection (2007, Kuruvilla et al. Virology 369:143-152), other studies reported frequencies below 20% of mice producing antigen-specific IgM and IgG after HIV and EBV infection (2006, Baenziger et al., Proc Natl Acad Sci USA 103:15951-15956; 2008, Yajima et al., J Infect Dis 198:673-682). Upon immunization with adjuvant and antigen, class switching of antigen-specific immunoglobulins is also historically inefficient with only a fraction of immunized animals showing antigen specific IgG responses (2004, Traggiai et al., Science 304:104-107; 2002, Ito et al., Blood 100:3175-3182; 2005, Ishikawa et al., Blood 106:1565-1573; 2005, Shultz et al., J Immunol 174:6477-6489; 2009, Watanabe et al., Int Immunol 21:843-858; 2010, Becker et al., PLoS ONE 5). These studies included NSG and BALB/c DKO mice and different adjuvant/antigen combinations.

There is a need in the art for non-human animals able to support and sustain engraftment with a human hematopoietic system. The present invention addresses this unmet need in the art.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A-1C, depicts the results of experiments assessing SIRPα expression. FIG. 1A depicts the analysis of mouse and human SIRPα (hSIRPα or huSIRPα) expression in the blood done by FACS staining in hSIRPα-transgenic and control animals. FIGS. 1B and 1C depict the clearance of human erythrocytes from −hSIRPα, +hSIRPα, and NSG mice.

FIG. 2, comprising FIG. 2A-2J, depicts the results of experiments examining the staining pattern and frequencies of particular cell types in mice after engraftment. FIGS. 2A through 2E depict the staining pattern and frequencies of $hCD45^+$, $hCD3^+$, $hCD19^+$, and $CD33^-$ $ssc^{low}$ cells in the blood as detected by FACS, 10 to 12 weeks after $CD34^+$ cell engraftment in different strains of mice. FIG. 2F through FIG. 2J depict the staining pattern, frequency of $hCD45^+$, and number of $CD45^+$, $hCD34^+$ progenitor cells, and $CD34^+$ $CD38^-$ cells in the bone marrow 12-14 weeks after $CD34^+$ engraftment in different strains of mice.

FIG. 3, comprising FIGS. 3A-3H, depict the results of experiments examining the staining pattern and frequencies of particular cell types in mice after engraftment. FIG. 3A through FIG. 3E depict the staining pattern, frequency, and number of $hCD45^+$ cells, $hCD3^+$ T cells, and $hCD19^+$ B cells in the spleen 12-14 weeks post transplantation into different mice strains. Further, FIG. 3F through FIG. 3H depict staining and cell number of $hCD45^+$ thymocytes and $hCD4^+CD8^+$ thymocytes in the thymus 12-14 weeks post transplantation into different mice strains.

FIGS. 4A-4I depict the results of experiments evaluating antibody producing cells and the production of antibodies in mice after engraftment. FIG. 4A through FIG. 4C depict total serum levels of IgM, IgG, and IgG producing cells in the spleen in −hSIRPα and +hSIRPα mice before immunization. FIG. 4D through FIG. 4I depict levels of anti-OVA IgM and IgG as detected by ELISA in −hSIRPα and +hSIRPα mice that were immunized with OVA.

FIGS. 5A-5D, depicts the results of experiments examining the expression of SIRPα and the quantification of particular cell types in −SIRPα and +SIRPα mice. FIG. 5A depicts the expression of mouse and human SIRPα in the spleen as analyzed by FACS staining in hSIRPα and control mice. FIG. 5B through FIG. 5D depict quantification of murine leukocytes (including neutrophils), red blood cells, and platelets in −SIRPα and +SIRPα mice.

FIG. 7 depicts the results of experiments evaluating the ratio of $CD4^-$ to $CD8^+$ T cells, frequency of $CD3^+CD4^+$ phenotypes, and frequencies of $hNKp46^+$ NK cells, $hCD33^+$ myeloid cells, and $hCD11c^+HLA-DR^+$ dendritic cells within the spleen 12-14 weeks after engraftment in the different mouse strains.

FIG. 8 depicts the frequency and number of $hCD45^+$ cells in the blood, and frequency and number of $hCD45^+$ cells, hCD19+ B cells, and hCD3+ T cells in the spleen at 3 months, 6 months, and 9 months post engraftment in the different mouse strains.

FIG. 9 depicts the phenotypic characterization of human B cells by showing the staining pattern and frequencies of CD10+ cells, CD10-CD27+ cells, CD138+CD38$^{high}$ cells, and CD138+CD38+/low cells in the bone marrow and spleen 12-14 weeks post engraftment in the different mouse strains.

DETAILED DESCRIPTION

Figure 1:
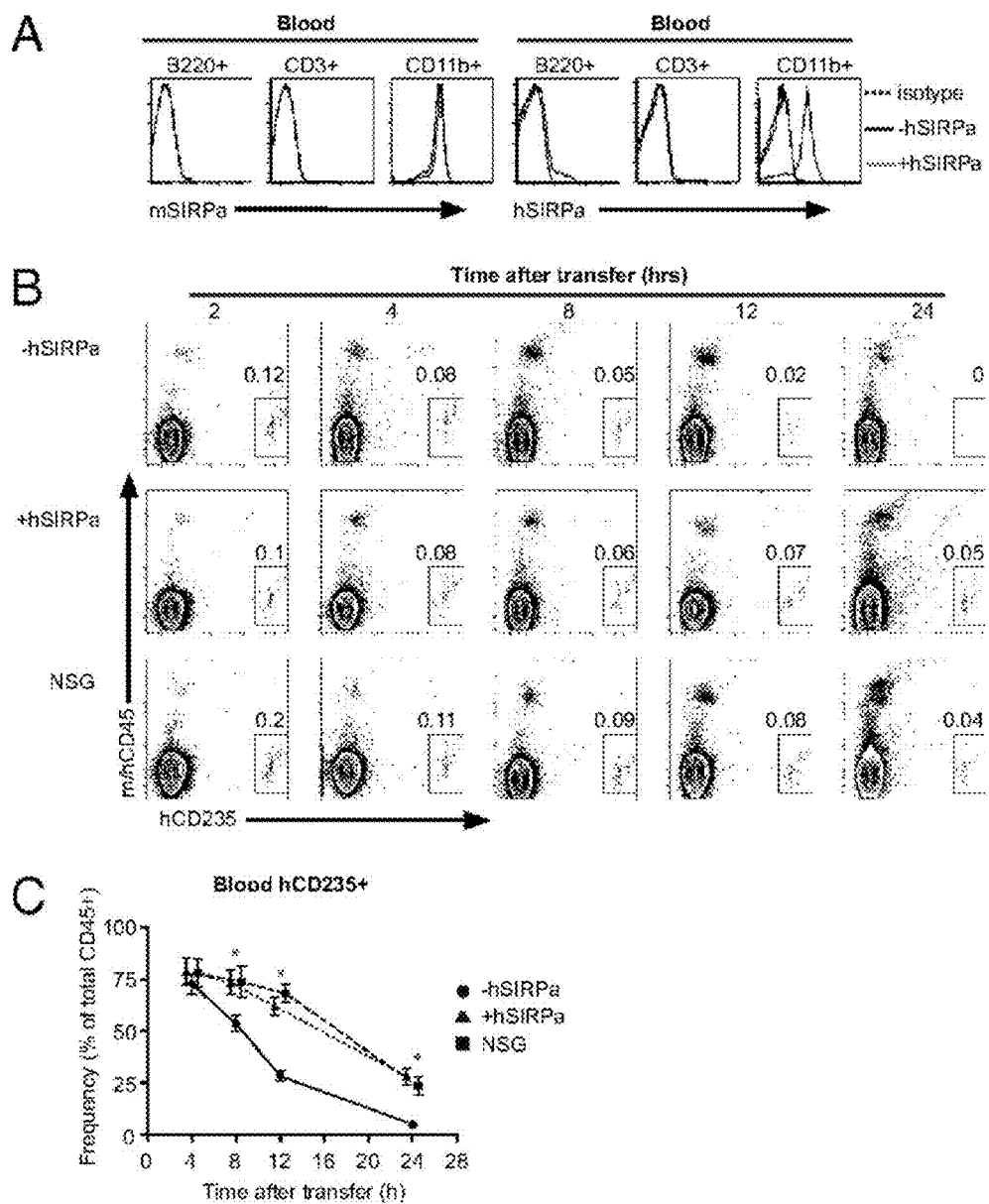
FIG. 1, comprising

The invention relates generally to compositions and methods of generating and using transgenic non-human animals expressing human SIRPα (hSIRPα or huSIRPα) that are engrafted with a human hematopoietic system. In various embodiments, the human hematopoietic system engrafted, +huSIRPα transgenic non-human animals of the invention are useful as systems for the in vivo evaluation of the growth and differentiation of hematopoietic and immune cells, for the in vivo assessment of an immune response, for the in vivo evaluation of vaccines and vaccination regimens, for the in vivo production and collection of immune mediators, including human antibodies, and for use in testing the effect of agents that modulate hematopoietic and immune cell function.

DEFINITIONS

Unless defined otherwise, all technical and scientific terms used herein have the same meaning as commonly understood by one of ordinary skill in the art to which this invention belongs. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; and Herdewijn, P. (Ed.), Oligonucleotide Synthesis: Methods and Applications, Methods in Molecular Biology, Humana Press, 2004. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

"Constitutive" expression is a state in which a gene product is produced in a living cell under most or all physiological conditions of the cell. A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The terms "expression construct" and "expression cassette" are used herein to refer to a double-stranded recombinant DNA molecule containing a desired nucleic acid huSIRPα coding sequence and containing one or more regulatory elements necessary or desirable for the expression of the operably linked coding sequence.

As used herein, the term "fragment," as applied to a nucleic acid or polypeptide, refers to a subsequence of a larger nucleic acid or polypeptide. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between). A "fragment" of a polypeptide can be at least about 15 nucleotides in length; for example, at least about 50 amino acids to about 100 amino acids; at least about 100 to about 500 amino acids, at least about 500 to about 1000 amino acids, at least about 1000 amino acids to about 1500 amino acids; or about 1500 amino acids to about 2500 amino acids; or about 2500 amino acids (and any integer value in between).

As used herein, the terms "gene" and "recombinant gene" refer to nucleic acid molecules comprising an open reading frame encoding a polypeptide. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

"Homologous" as used herein, refers to the subunit sequence similarity between two polymeric molecules, e.g. between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g. if half (e.g., five positions in a polymer ten subunits in length) of the positions in two compound sequences are homologous then the two sequences are 50% homologous, if 90% of the positions, e.g. 9 of 10, are matched or homologous, the two sequences share 90% homology. By way of example, the DNA sequences 5'-ATTGCC-3' and 5'-TATGGC-3' share 75% homology.

The terms "human hematopoietic stem cell and progenitor cells" and "human HSPC" as used herein, refer to human multipotent hematopoietic stem cells and hematopoietic progenitor cells.

"Inducible" expression is a state in which a gene product is produced in a living cell in response to the presence of a signal in the cell.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

The term "operably linked" as used herein refers to a polynucleotide in functional relationship with a second polynucleotide. By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized, upon the other. By way of example, a promoter operably linked to the coding region of a gene is able to promote transcription of the coding region. Preferably, when the nucleic acid encoding the desired protein further comprises a promoter/regulatory sequence, the promoter/regulatory sequence is positioned at the 5' end of the desired protein coding sequence such that it drives expression of the desired protein in a cell. Together, the nucleic acid encoding the desired protein and its promoter/regulatory sequence comprise a "transgene."

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof. The term "peptide" typically refers to short polypeptides. The term "protein" typically refers to large polypeptides.

The term "progeny" as used herein refers to a descendent or offspring and includes the differentiated or undifferentiated decedent cell derived from a parent cell. In one usage, the term progeny refers to a descendent cell which is genetically identical to the parent. In another use, the term progeny refers to a descendent cell which is genetically and phenotypically identical to the parent. In yet another usage, the term progeny refers to a descendent cell that has differentiated from the parent cell.

The term "promoter" as used herein refers to a DNA sequence operably linked to a nucleic acid sequence to be transcribed such as a nucleic acid sequence encoding a desired molecule. A promoter is generally positioned upstream of a nucleic acid sequence to be transcribed and provides a site for specific binding by RNA polymerase and other transcription factors. In specific embodiments, a promoter is generally positioned upstream of the nucleic acid sequence transcribed to produce the desired molecule, and provides a site for specific binding by RNA polymerase and other transcription factors. An included promoter can be a constitutive promoter or can provide inducible expression; and can provide ubiquitous, tissue-specific or cell-type specific expression.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

A "recombinant polypeptide" is one, which is produced upon expression of a recombinant polynucleotide.

The term "regulatory element" as used herein refers to a nucleotide sequence which controls some aspect of the expression of nucleic acid sequences. Exemplary regulatory elements illustratively include an enhancer, an internal ribosome entry site (IRES), an intron; an origin of replication, a polyadenylation signal (pA), a promoter, an enhancer, a transcription termination sequence, and an upstream regulatory domain, which contribute to the replication, transcription, post-transcriptional processing of a nucleic acid sequence. Those of ordinary skill in the art are capable of selecting and using these and other regulatory elements in an expression construct with no more than routine experimentation. Expression constructs can be generated recombinantly or synthetically using well-known methodology.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific.

In some instances, the terms "specific binding" or "specifically binding", can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

As used herein, the term "transgenic" means an animal, the germ cells of which, comprise an exogenous nucleic acid.

Description

The invention relates generally to compositions and methods of generating and using transgenic non-human animals expressing human SIRPα (hSIRPα or huSIRPα) that are engrafted with a human hematopoietic system. In various embodiments, the human hematopoietic system engrafted, +huSIRPα transgenic non-human animals of the invention are useful as systems for the in vivo evaluation of the growth and differentiation of hematopoietic and immune cells, for the in vivo assessment of an immune response, for the in vivo evaluation of vaccines and vaccination regimens, for the in vivo production and collection of immune mediators, including human antibodies, and for use in testing the effect of agents that modulate hematopoietic and immune cell function.

Transgenic Animals

The invention includes a transgenic non-human animal that expresses huSIRPα. In some embodiments, the transgenic non-human animal expressing huSIRPα also expresses a non-human SIRPα. In other embodiments, the transgenic non-human animal expressing huSIRPα does not also express a non-human SIRPα. In some embodiments the huSIRPα transgenic animal is an animal having one or more genes knocked out to render the animal an immunodeficient animal, as elsewhere described herein. To create a transgenic animal, a nucleic acid encoding the huSIRPα protein can be incorporated into a recombinant expression vector in a form suitable for expression of the huSIRPα protein in a non-human host cell. In various embodiments, the recombinant expression vector includes one or more regulatory sequences operatively linked to the nucleic acid encoding the huSIRPα protein in a manner which allows for transcription of the nucleic acid into mRNA and translation of the mRNA into the huSIRPα protein. The term "regulatory sequence" is art-recognized and intended to include promoters, enhancers and other expression control elements (e.g., polyadenylation signals). Such regulatory sequences are known to those skilled in the art and are described in 1990, Goeddel, Gene Expression Technology: Methods in Enzymology 185, Academic Press, San Diego, Calif. It should be understood that the design of the expression vector may depend on such factors as the choice of the host cell to be transfected and/or the amount of huSIRPα protein to be expressed.

A transgenic animal can be created, for example, by introducing a nucleic acid encoding the huSIRPα protein (typically linked to appropriate regulatory elements, such as a constitutive or tissue-specific enhancer) into an oocyte, e.g., by microinjection, and allowing the oocyte to develop in a female foster animal. Intronic sequences and polyadenylation signals can also be included in the transgene to increase the efficiency of expression of the transgene. Methods for generating transgenic animals, particularly animals such as mice, have become conventional in the art and are described, for example, in U.S. Pat. Nos. 4,736,866 and 4,870,009 and 1986, Hogan et al., A Laboratory Manual, Cold Spring Harbor, N.Y., Cold Spring Harbor Laboratory. A transgenic founder animal can be used to breed additional animals carrying the transgene. Transgenic animals carrying a transgene encoding the huSIRPα protein of the invention can further be bred to other transgenic animals carrying other transgenes, or be bred to knockout animals, e.g., a knockout animal that does not express one or more of its genes. In various embodiments, the transgenic animal of the invention is a mouse, a rat or a rabbit.

In one embodiment, the transgenic animal of the invention expresses huSIRPα from the native huSIRPα promoter and its native regulatory elements, but the skilled artisan will understand that the transgenic animal of the invention encompasses the expression of huSIRPα from other promoters and enhancers. Examples of promoters useful in the invention include, but are not limited to, DNA pol II promoter, PGK promoter, ubiquitin promoter, albumin promoter, globin promoter, ovalbumin promoter, SV40 early promoter, the Rous sarcoma virus (RSV) promoter, retroviral LTR and lentiviral LTR. Promoter and enhancer expression systems useful in the invention also include inducible and/or tissue-specific expression systems.

In some embodiments, the invention includes transgenic immunodeficient animals having a genome that includes a nucleic acid encoding huSIRPα operably linked to a promoter, wherein the animal expresses the encoded huSIRPα. In various embodiments, the invention includes transgenic immunodeficient non-human animals having a genome that comprises an expression cassette that includes a nucleic acid encoding huSIRPα, wherein the nucleic acid is operably linked to a promoter and a polyadenylation signal and further contains an intron, and wherein the animal expresses the encoded huSIRPα polypeptide.

In various embodiments, various methods are used to introduce a huSIRPα transgene into an immunodeficient animal to produce a transgenic immunodeficient animal that expresses huSIRPα. Such techniques are well-known in the art and include, but are not limited to, pronuclear microinjection and transformation of embryonic stem cells. Methods for generating transgenic animals that can be used include, but are not limited to, those described in Sundberg and Ichiki (2006, Genetically Engineered Mice Handbook, CRC Press), Hofker and van Deursen (2002, Transgenic Mouse Methods and Protocols, Humana Press), Joyner (2000, Gene Targeting: A Practical Approach, Oxford University Press), Turksen (2002, Embryonic stem cells: Methods and Protocols in Methods Mol Biol., Humana Press) and Meyer et al. (2010, Proc. Nat. Acad. Sci. USA 107:15022-15026).

In some embodiments, the compositions and methods of the invention comprise transgenic immunodeficient animals deficient in B cell and/or T cell number and/or function, alone, or in combination with, an IL2 receptor gamma chain deficiency, and having a genome that comprises a nucleic acid encoding huSIRPα operably linked to a promoter, wherein the animal expresses the encoded huSIRPα polypeptide. The generation of the +huSIRPα transgenic animal of the invention can be achieved by methods such as DNA injection of an expression construct into a preimplantation embryo or by use of stem cells, such as embryonic stem (ES) cells or induced pluripotent stem (iPS) cells.

In one embodiment, SIRPα is expressed by the native regulatory elements of huSIRPα. In other embodiments, SIRPα is expressed from a ubiquitous promoter. Nonlimiting examples of ubiquitous promoters useful in the expression construct of the compositions and methods of the invention include, a 3-phosphoglycerate kinase (PGK-1) promoter, a beta-actin promoter, a ROSA26 promoter, a heat shock protein 70 (Hsp70) promoter, an EF-1 alpha gene encoding elongation factor 1 alpha (EF1) promoter, an eukaryotic initiation factor 4A (eIF-4A1) promoter, a chloramphenicol acetyltransferase (CAT) promoter and a CMV (cytomegalovirus) promoter.

In other embodiments, SIRPα is expressed from a tissue-specific promoter. Nonlimiting examples of tissue-specific promoters useful in the expression construct of the compositions and methods of the invention include a promoter of a gene expressed in the hematopoietic system, such as an SIRPα promoter, an IFN-β promoter, a Wiskott-Aldrich syndrome protein (WASP) promoter, a CD45 (also called leukocyte common antigen) promoter, a Flt-1 promoter, an endoglin (CD105) promoter and an ICAM-2 (Intracellular Adhesion Molecule 2) promoter. These and other promoters useful in the compositions and methods of the invention are known in the art as exemplified in Abboud et al. (2003, J. Histochem & Cytochem. 51:941-949), Schorpp et al. (1996, NAR 24:1787-1788), McBurney et al. (1994, Devel. Dynamics, 200:278-293) and Majumder et al. (1996, Blood 87:3203-3211). Further to comprising a promoter, one or more additional regulatory elements, such as an enhancer element or intron sequence, is included in various embodiments of the invention. Examples of enhancers useful in the compositions and methods of the invention include, but are not limited to, a cytomegalovirus (CMV) early enhancer element and an SV40 enhancer element. Examples of intron sequences useful in the compositions and methods of the invention include, but are not limited to, the beta globin intron or a generic intron. Other additional regulatory elements useful in some embodiments of the invention include, but are not limited to, a transcription termination sequence and an mRNA polyadenylation (pA) sequence.

In some embodiments, the methods of DNA injection of an expression construct into a preimplantation embryo include linearization of the expression construct before it is injected into a preimplantation embryo. In preferred embodiments, the expression construct is injected into fertilized oocytes. Fertilized oocytes can be collected from superovulated females the day after mating and injected with the expression construct. The injected oocytes are either cultured overnight or transferred directly into oviducts of 0.5-day p.c. pseudopregnant females. Methods for superovulation, harvesting of oocytes, expression construct injection and embryo transfer are known in the art and described in Manipulating the Mouse Embryo (2002, A Laboratory Manual, 3rd edition, Cold Spring Harbor Laboratory Press). Offspring can be evaluated for the presence of the introduced transgene by DNA analysis (e.g., PCR, Southern blot, DNA sequencing, etc.) or by protein analysis (e.g., ELISA, Western blot, etc.).

In other embodiments, the expression construct may be transfected into stem cells (ES cells or iPS cells) using well-known methods, such as electroporation, calcium-phosphate precipitation and lipofection. The cells can be evaluated for the presence of the introduced transgene by DNA analysis (e.g., PCR, Southern blot, DNA sequencing, etc.) or by protein analysis (e.g., ELISA, Western blot, etc.). Cells determined to have incorporated the expression construct can then be microinjected into preimplantation embryos. For a detailed description of methods known in the art useful for the compositions and methods of the invention, see Nagy et al., (2002, Manipulating the Mouse Embryo: A Laboratory Manual, 3rd edition, Cold Spring Harbor Laboratory Press), Nagy et al. (1990, Development 110:815-821), U.S. Pat. No. 7,576,259, U.S. Pat. No. 7,659,442, U.S. Pat. No. 7,294,754, and Kraus et al. (2010, Genesis 48:394-399).

The +huSIRPα transgenic animals can be crossed to immunodeficient animal to create an immunodeficient animal expressing huSIRPα transgene. Various embodiments of the invention provide transgenic animals that include a huSIRPα transgene in substantially all of their cells, as well as transgenic animals that include a huSIRPα transgene in some, but not all their cells. One or multiple copies, adjacent or distant to one another, of the huSIRPα transgene may be integrated into the genome of the cells of the transgenic animals.

In some embodiments, the invention is a method of engrafting human hematopoietic stem cell and progenitor cells (HSPCs) in an immunodeficient, +huSIRPα transgenic animal. Engraftment of human hematopoietic stem cell and progenitor cells in the immunodeficient, +huSIRPα transgenic animal of the invention is characterized by the presence of differentiated human hematopoietic cells in the engrafted animal in which huSIRPα is provided to the human hematopoietic stem cell and progenitor cells. In particular embodiments, engraftment of human hematopoietic stem cell and progenitor cells in an immunodeficient animal is characterized by greater numbers of differentiated human hematopoietic cells in the engrafted animal in which huSIRPα is provided to human hematopoietic stem cell and progenitor cells, as compared with appropriate control animals in which huSIRPα is not provided to the human hematopoietic stem cell and progenitor cells.

The methods and transgenic immunodeficient animals provided in various embodiments of the present invention have various utilities such as, but not limited to, for use as models of growth and differentiation of immune cells, for in vivo study of an immune response, for in vivo evaluation of vaccines and vaccination regimens, for in vivo production and collection of immune mediators, such as an antibody, and for use in testing the effect of agents that affect hematopoietic and immune cell function.

Engraftment of human HSPC in immunodeficient animals has traditionally required conditioning prior to administration of the HSPC, either sub-lethal irradiation of the recipient animal with high frequency electromagnetic radiation, generally using gamma radiation, or treatment with a radiomimetic drug such as busulfan or nitrogen mustard. Conditioning is believed to reduce numbers of host hematopoietic cells, create appropriate microenvironmental factors for engraftment of human HSPC, and/or create microenvironmental niches for engraftment of human HSPC. Standard methods for conditioning are known in the art, such as described herein and in J. Hayakawa et al, 2009, Stem Cells, 27(1):175-182. Methods for engraftment of human hematopoietic stem cell and progenitor cells in immunodeficient animals are provided according to embodiments of the present invention which include providing huSIRPα to the human HSPC in the immunodeficient animals, with or without irradiating the animals prior to administration of the HSPC. Methods for engraftment of human hematopoietic stem cell and progenitor cells in immunodeficient animals are provided according to embodiments of the present invention which include providing huSIRPα to the human HSPC in the immunodeficient animals, with or without, administering a radiomimetic drug, such as busulfan or nitrogen mustard, to the animals prior to administration of the HSPC.

In some embodiments, the methods of HSPC engraftment in an immunodeficient animal according to embodiments of the present invention include providing huSIRPα to human HSPC in an immunodeficient animal. In some embodiments, the immunodeficient animal is deficient in B cell and/or T cell number and/or function. In other embodiments, the immunodeficient animal has severe combined immune deficiency (SCID). SCID refers to a condition characterized by the absence of T cells and lack of B cell function. Examples of SCID include: X-linked SCID, which is characterized by gamma chain gene mutations in the IL2RG gene and the lymphocyte phenotype T(−) B(+) NK(−); and autosomal recessive SCID characterized by Jak3 gene mutations and the lymphocyte phenotype T(−) B(+) NK(−), ADA gene mutations and the lymphocyte phenotype T(−) B(−) NK(−), IL-7R alpha-chain mutations and the lymphocyte phenotype T(−) B(+) NK(+), CD3 delta or epsilon mutations and the lymphocyte phenotype T(−) B(+) NK(+), RAG1/RAG2 mutations and the lymphocyte phenotype T(−) B(−) NK(+), Artemis gene mutations and the lymphocyte phenotype T(−) B(−) NK(+), CD45 gene mutations and the lymphocyte phenotype T(−) B(+) NK(+).

In some embodiments, the methods of HSPC engraftment in a immunodeficient, +huSIRPα transgenic animal according to embodiments of the present invention include providing huSIRPα to human HSPC in a mouse having the severe combined immunodeficiency mutation (Prkdc$^{scid}$), commonly referred to as the scid mutation. The scid mutation is well-known and located on mouse chromosome 16 as described in Bosma et al. (1989, Immunogenetics 29:54-56). Mice homozygous for the scid mutation are characterized by an absence of functional T cells and B cells, lymphopenia, hypoglobulinemia and a normal hematopoietic microenvironment. The scid mutation can be detected, for example, by detection of markers of the scid mutation using well-known methods.

In other embodiments, the methods of HSPC engraftment in an immunodeficient animal according to embodiments of the present invention include providing huSIRPα to human HSPC in an immunodeficient mouse having an IL2 receptor gamma chain deficiency, either alone, or in combination with, the severe combined immunodeficiency (scid) mutation. The term "IL2 receptor gamma chain deficiency" refers to decreased IL2 receptor gamma chain. Decreased IL2 receptor gamma chain can be due to gene deletion or mutation. Decreased IL2 receptor gamma chain can be detected, for example, by detection of IL2 receptor gamma chain gene deletion or mutation and/or detection of decreased IL2 receptor gamma chain expression using well-known methods.

In preferred embodiments, huSIRPα is provided by expression of a nucleic acid encoding SIRPα in the immunodeficient animal. In various embodiments, the transgenic immunodeficient animal of the invention expresses a huSIRPα from a nucleic acid encoding the huSIRPα, incorporated into some or all of the cells of the animal. In addition to the naturally occurring huSIRPα nucleic acid and amino acid sequences, the term huSIRPα encompasses variants of huSIRPα which may be delivered to an immunodeficient animal according to embodiments of methods of the present invention. As used herein, the term "variant" defines either an isolated naturally occurring genetic mutant of a huSIRPα or a recombinantly prepared variation of a huSIRPα, each of which contain one or more mutations compared with the corresponding wild-type huSIRPα. For example, such mutations can be one or more amino acid substitutions, additions, and/or deletions. The term "variant" also includes non-human SIRPα orthologues. In some embodiments, a variant SIRPα protein of the present invention has at least 90%, 91%, 92%, 93%, 94%, 95%, 96%, 97%, 98% or 99% identity to wild-type huSIRPα.

The percent identity between two sequences is determined using techniques as those described elsewhere herein. Mutations can be introduced using standard molecular biology techniques, such as site-directed mutagenesis and PCR-mediated mutagenesis. One of skill in the art will recognize that one or more amino acid mutations can be introduced without altering the functional properties of huSIRPα proteins.

Conservative amino acid substitutions can be made in huSIRPα proteins to produce huSIRPα protein variants. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

Human SIRPα variants can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, methylhistidine, and ornithine.

Human SIRPα variants are encoded by nucleic acids having a high degree of identity with a nucleic acid encoding a wild-type huSIRPα. The complement of a nucleic acid encoding a huSIRPα variant specifically hybridizes with a nucleic acid encoding a wild-type huSIRPα under high stringency conditions.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide in a single-stranded form of nucleic acid.

Nucleic acids encoding SIRPα or a SIRPα variant can be isolated or generated recombinantly or synthetically using well-known methodology.

Isolation of human HSPC, administration of the human HSPC to a host organism and methods for assessing engraftment thereof are well-known in the art. Hematopoietic stem cell and progenitor cells for administration to an immunodeficient animal can be obtained from any tissue containing HSPC such as, but not limited to, umbilical cord blood, bone marrow, peripheral blood, GM-CSF-mobilized peripheral blood and fetal liver. HSPC can be administered into newborn or adult immunodeficient animals by administration via various routes, such as, but not limited to, intravenous, intrahepatic, and intraperitoneal.

Engraftment of human HSPC in the +huSIRPα transgenic immunodeficient animal of the invention can be assessed by any of various methods, such as, but not limited to, flow cytometric analysis of cells in the animals to which the human HSPC are administered at one or more time points following the administration of HSPC.

Exemplary methods of isolating human HSPC, of administering human HSPC to a host animal, and of assessing engraftment of the human HSPC in the host animal are described herein and in Pearson et al. (2008, Curr. Protoc. Immunol. 81:1-15), Ito et al. (2002, Blood 100:3175-3182), Traggiai et al. (2004, Science 304:104-107), Ishikawa et al. (2005, Blood 106:1565-1573), Shultz et al. (2005, J. Immunol. 174:6477-6489) and Holyoake et al. (1999, Exp Hematol. 27:1418-27).

In various embodiments of the invention, the human HSPC are isolated from an original source material to obtain a population of cells enriched in HSPCs. The isolated HSPCs may or may not be pure. In one embodiment, HSPCs useful in the compositions and methods of the invention are enriched by selection for a marker, such as CD34. In some embodiments, HSPCs useful in the compositions and methods of the invention are a population of cells in which CD34+ cells constitute about 1-100% of the cells, although in certain embodiments, a population of cells in which CD34+ cells constitute fewer than 1% of total cells can also be used. In certain embodiments, the HSPCs useful in the compositions and methods of the invention are a T cell-depleted population of cells in which CD34+ cells make up about 1-3% of total cells, a lineage-depleted population of cells in which CD34+ cells make up about 50% of total cells, or a CD34+ positive selected population of cells in which CD34+ cells make up about 90% of total cells.

The number of HSPCs administered is not considered limiting with regard to generation of a human hematopoietic and immune system in an immunodeficient mouse expressing SIRPα. A single HSPC is able to generate an entire hematopoietic system. Thus, the number of HSPCs administered is generally in the range of about $3 \times 10^3$ to $1 \times 10^6$ CD34+ cells when the recipient is a mouse, although in various embodiments, more or fewer can also be used. For other species of recipient, the number of cells that need to be administered can be determined using only routine experimentation.

Generally, engraftment is considered successful when the administered human HSPCs, and progeny of the administered human HSPCs, in the recipient animal are detected at a time when administered non-HSPC are no longer readily detectable. Detection of the progeny of the administered HSPC cells can be achieved by detection of human DNA in the recipient animal, for example, or by detection of intact human HSPCs and cells differentiated from the HSPCs, for example. Serial transfer of human CD34+ cells from a first recipient into a secondary recipient, and engraftment of a human hematopoietic system in the second recipient, is a further optional test of HSPC engraftment in the primary recipient. Engraftment can be detected by flow cytometry as 0.05% or greater human CD45+ cells in the blood, spleen or bone marrow at 2-4 months after administration of the human HSPC. A cytokine (e.g., GM-CSF) can be used to mobilize stem cells, for example, as described in Watanabe (1997, Bone Marrow Transplantation 19:1175-1181).

Human Antibody Production

The invention also comprises compositions and methods useful for the production of human monoclonal antibodies from an engrafted immunodeficient animal, as elsewhere described herein. In various embodiments, the methods comprise contacting an immunodeficient animal with a human hematopoietic stem cell and progenitor cell to generate an immune system-transplanted non-human animal (engrafted animal), subsequently contacting the engrafted animal with an antigen, collecting from the engrafted animal a human cell producing a human antibody against the antigen, and isolating the antibody from the antibody producing cell.

In various embodiments, the invention comprises a method that includes establishing an antibody producing cell (e.g., a human B-cell) by a transformation method (e.g. EBV) or a cell fusion method (e.g. hybridoma). Preferably the antibody producing cell is capable of being maintained under suitable cell culture conditions for at least about 50 passages.

In various embodiments, the engrafted animal is a non-human mammal. In some embodiments, the engrafted animal is a mouse, rat or a rabbit. It is further preferred that the mouse is a transgenic $Rag2^{-/-}\gamma c^{-/-}$ knockout mouse expressing huSIRPα.

In various embodiments of the invention, the human hematopoietic stem cell and progenitor cell (HSPC) is CD34+ cell obtained from a human fetal liver, bone marrow, cord blood, peripheral blood, or spleen sample.

In various embodiments, the antigen is at least one of: a peptide, a polypeptide, an MHC/peptide complex, DNA, a live virus, a dead virus or portion thereof, a live bacteria, a dead bacteria or portion thereof, or a cancer cell or portion thereof.

In some embodiments, the engrafted animal has been contacted with the antigen 1-5 months after the animal has been contacted with the human hematopoietic stem cell and progenitor cell. In some embodiments, the engrafted animal is contacted only one time with the antigen, while in other embodiments, the engrafted animal is contacted two, three, four, five, six, seven, eight, or more times with the antigen.

In one embodiment, human antibody producing cell collected from the engrafted animal is a B cell. In various embodiments, the human antibody producing cell collected from the animal expresses on its surface at least one of: CD19, CD20, CD22, and CD27. The human antibody-producing cell of the invention can be recovered by removal of any suitable cellular components of the immune system from the animal. In various embodiments, the antibody-producing cell is removed from the engrafted animal by removal of at least one of the spleen, the lymph nodes, the peripheral blood, the bone marrow or portions thereof.

In various embodiments, the method of the invention employs a conventional hybridoma technology using a suitable fusion partner. In various embodiments, the fusion partner is at least one cell selected from the group consisting of: MOPC21, P3X63AG8, SP2/0, NS-1, P3.X63AG8.653, F0, S194/5.XXO.BU-1, FOX-NY, SP2/0-Ag14, MEG-01, HEL, UT-7, M07e, MEG-A2, and DAMI, and cell lines derived from these cells.

Methods of isolating an antibody from the engrafted animal of the invention are well known in the art. Isolation of the antibody from the antibody producing cell, the media in which the antibody producing cell is culture, and/or the ascites of the engrafted animal, can be performed according to the methods known in the art, such as, by way of example, chromatography and dialysis. In other various embodiments, the antibody can be isolated using one or more of immunoaffinity purification, ammonium sulphate precipitation, protein A/G purification, ion exchange chromatography and gel filtration. Such methods are described in Nau (1989, Optimization of monoclonal antibody purification, In: Techniques in Protein Chemistry, Hugli, T. (ed.), Academic Press, New York) and Coligan et al. (2005, Current Protocols in Immunology, John Wiley & Sons, Inc.).

The antigen may be administered to the engrafted animal by any suitable means known in art. In various embodiments, the antigen can be administered to the engrafted animal by at least one of intrasplenically, intravenously, intraperitoneally, intradermally, intramuscularly, and subcutaneously. In some embodiments, the antigen is administered alone and in other embodiments, the antigen is administered in combination with appropriate immunomodulating agent or adjuvant. Examples of adjuvants useful in the methods of the invention include, but are not limited to, Complete Freund's Adjuvant (CFA), Incomplete Freund's Adjuvant (IFA), and Alum $(Al_3(OH)_4)$.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.

Materials and Methods

Generation of Human SIRPα-Transgenic Mice

To generate a mouse expressing the huSIRPα gene, a bacterial artificial chromosome (BAC) clone spanning the huSIRPα locus was obtained (from BACPACCHORI, http://bacpac.chori.org/). This clone (RP1179H23, accession number A6083837) is 177 kb in length and contains the entire 45-kb SIRPα gene along with ~51 kb of flanking DNA on the 5' end and 78 kb on the 3' end. Sequencing revealed that the SIRPα allele corresponds to variant 2 described in Takenaka et al. (2007, Nat Immunol 8: 1313-23). A hygromycin selectable marker was then inserted by homologous recombination into the middle of intron 1 within the gene in a 2-kb region lacking repetitive elements and any significant sequence conservation between mouse and human.

The selection cassette contains a hygromycin coding region driven by both a small bacterial Em7 promoter and a human ubiquitin C promoter, with a phosphoglycerate kinase 3' region providing transcription termination and poly(A) addition signals. The cassette is flanked with 34-bp loxP sites for recombinational excision at the embryonic stem (ES) cell stage by means of Cre recombinase. Two selected 400-bp PCR-amplified segments from the huSIRPα intron (homology boxes A and B) were then appended to the 3-kb hygromycin cassette by ligation, and the resultant 3.8-kb product was PCR amplified for subsequent recombinational insertion. E. coli DH10 cells containing the huSIRPα BAC were made recombination proficient by the introduction and subsequent induction of an abg expression plasmid.

The hygromycin cassette flanked by SIRPα homology boxes was then electroporated into the recombination-proficient BAC host and plated on medium containing both chloramphenicol and hygromycin to select for both the BAC vector and the hygromycin insert. Correct, site-specific insertion was detected by the PCR amplification of unique junction fragments at the boundaries of the insertion site. The recombined SIRPα genomic segment of 177 kb was excised from the BAC vector by NotI digestion, and the DNA was then introduced into $F_1$ 129/BALB/c Rag2$^{+/-}$γc$^{y/-}$ ES cells by electroporation, followed by selection with hygromycin. Resistant clones were screened for huSIRPα sequences by PCR. Selected clones with the largest genomic flanking regions were subjected to karyotype analysis and then microinjected into d3.5pc C57BL/6 blastocysts. Chimeric mice were genotyped using the same primer sets as for the ES cells. To obtain huSIRPα-transgenic Rag2$^{-/-}$γc$^{-/-}$ mice, chimeric Rag2$^{+/-}$γc$^{y/-}$ mice were crossed once with Rag2$^{-/-}$γc$^{-/-}$. For all experiments, hSIRPα transgenic and littermate control mice were used.

Preparation of Humanized Mice

Human fetal liver was obtained from the Fetal Tissue Bank at the Albert Einstein College, NY and from Advanced Bioscience Resources, CA. The tissue was minced and treated with 2 mg/mL collagenase D (Roche Diagnostics, IN) in HBSS with $CaCl_2/MgCl_2$ for 30 min at room temperature followed by filtering through 70-µm nylon cell strainers (BD Biosciences, CA). Human CD34$^+$ cells were isolated using the direct CD34 MicroBead Kit (Miltenyi Biotec, CA) and subsequently cryopreserved. NOD/scid/gc mice were obtained from The Jackson Laboratory and bred in our animal facility. All mice were maintained on a 2-wk on/off schedule of sulfatrim, whereas NSG mice received additionally baytril during the weeks without sulfatrim. Newborn mice (1-3 d old) were irradiated twice with 180 cGy (Rag2$^{-/-}$γc$^{-/-}$ mice) or once with 100 cGy (NSG) and injected intrahepatically with 1-2×10^5 CD34$^-$ HPCs post irradiation. The mice were bled 9-12 wk post engraftment, and peripheral lymphocytes were analyzed by FACS as described (2005, Shultz et al., J Immunol 174:6477-89; 2009, Strowig et al., J Exp Med 206:1423-34) to check for the reconstitution of the human immune system. Animal protocols were approved by the Institutional Animal Care and Use Committee of Yale University.

Monoclonal Antibodies and Flow Cytometry

Analysis of cell surface markers was performed using monoclonal Abs from BD Biosciences, eBioscience, and Biolegend. The following anti-mouse antibodies were used: mSIRPα (clone: P84), B220 (RAR-6B2), mCD3 (145-2C11), mCD11b (M1/70), mCD11c (HL3), and mCD45 (30-F11). The following anti-human antibodies were used: hCD45 (clone: HI30), hSIRPα (SE5A5), hCD3 (UCHT1), hNKp46 (9E2), hCD19 (SJ25C1), hCD27 (O323), hCD45RO (UCHL1), hCCR7 (3D12), hCD34 (581), hCD38 (HB7), hCD138 (MI15), hCD66 (B1.1/CD66), hCD33 (WM53), hCD11c (B-ly6), aHLA-DR (L243), hCD4 (RPA-T4), hCD8 (HIT8a), hCD235 (GA-R2), hCD41 (HIP8), and hCD10 (HI10a). For direct labeling, cells were stained in FACS buffer containing 2% FCS, 2mMEDTA, and 10 µg/mL FcR blocking antibody (clone 2.4G2). Cells were then washed, and flow cytometric analysis was performed on an LSRII (BD Biosciences). Data were analyzed using FlowJo.

Immunization of Humanized Mice

For immunization, 100 µg of ovalbumin (Sigma-Aldrich) in 100 µl of PBS were mixed with an equal volume of Complete Freund's Adjuvant (Difco). Twelve- to 14-wk-old humanized mice were immunized by intraperitoneal injection. Two weeks later, mice were boosted with 100 µg of ovalbumin in 100 µl of PBS mixed with an equal volume of Incomplete Freund's Adjuvant. Ten to 14 d later, mice were bled to analyze levels of antigen-specific immunoglobulins.

Analysis of Total Human Immunoglobulin Levels

Levels of human IgM and IgG were determined by ELISA. Multisorp plates (NUNC) were coated overnight at 4° C. with rabbit polyclonal antihuman IgM or IgG (Southern Biotech). After washing the wells once with 0.05% Tween 20/PBS, wells were blocked with 2% BSA in PBS for 1 h. After washing twice with 0.05% Tween 20/PBS, diluted samples were applied to wells for 2 h at room temperature. Human serum with known concentrations of IgM and IgG (Bethyl Laboratories) was used as a standard. After washing three times with 0.05% Tween 20/PBS, biotinylated rabbit polyclonal anti-human IgM or IgG was added for 1 h at room temperature. After washing four times with 0.05% Tween 20/PBS, streptavidin-HRP was added for 1 h at room temperature. After washing four times with 0.05% Tween 20/PBS, ELISAs were developed using TMB, and the reaction was stopped using Stop solution. Plates were analyzed using a Bio-Rad plate reader.

Analysis of Antigen-Specific Ig Levels

Levels of ovalbumin-specific antibodies were determined similar to total Ig levels with a single change. Plates were coated with 100 µg/mL ovalbumin in PBS overnight at 4° C. instead of anti-human IgM/IgG antibodies.

Statistical Analysis

Statistical analyses were performed using the Graph-Pad Prism v. 4.00 for Macintosh (GraphPad Software, San Diego, Calif.). If not otherwise indicated, statistical significance was evaluated by one-way ANOVA using a Bonferroni post hoc test. In instances in which results did not follow a normal distribution, a Mann-Whitney test was used.

The results of the experiments are now described.

The results described herein demonstrate that transgenic, faithful expression of huSIRPα in mice is sufficient to strongly decrease rejection of human cells in Rag2$^{-/-}$γc$^{-/-}$ on a mixed 129/BALB/c background, resulting in increased human cell numbers and an increased functionality of the human adaptive immune system in vivo. In the initial experiments to evaluate whether hSIRPα is functional in transgenic mice, human erythrocytes were transferred into mice. This approach was chosen because negative regulation of erythrophagocytosis is highly dependent on the interaction of CD47 and SIRP (2000, Oldenborg et al., Science 288:2051-2054). Human erythrocytes were cleared within hours in DKO mice and the decreased clearance of erythrocytes in hSIRPα-DKO mice compared with DKO mice indicates that hSIRPα is able to negatively regulate phagocytosis by murine macrophages and that human erythrocyte clearance is indeed modulated via CD47-SIRPα interaction. However, not only phagocytosis of erythrocytes is regulated by this interaction, as also murine CD47$^{-/-}$ leukocytes are rapidly cleared upon transfer into WT mice, leading to a failure of CD47$^{-/-}$ cells to repopulate lethally irradiated mice (2001, Blazar et al., J Exp Med 194:541-549). Moreover, in wild-type mice, circulating murine HSPCs up-regulate CD47 to avoid phagocytosis in the spleen, demonstrating a requirement for HSPC survival (2009, Jaiswal et al., Cell 138:271-285). In line with these findings, it is demonstrated herein that expression of hSIRPα in 129/BALB/c Rag2$^{-/-}$γc$^{-/-}$ mice enhanced the efficiency of engraftment of human hematopoietic stem and progenitor cells at two levels. First, the frequency of mice with detectable human cell engraftment in the peripheral blood was almost doubled, and second, frequencies of human cell engraftment were significantly increased. In comparison with NSG mice, hSIRPα-DKO mice were equally well engrafted, but a slightly increased early mortality (<12 wk) of engrafted NSG mice was observed, which can likely be attributed to increased gamma-irradiation sensitivity of scid strains compared with Rag1/Rag2-deficient strains. The analysis of hematopoietic organs in the different strains of mice demonstrate increased numbers of human HSPCs in the bone marrow of hSIRPα-DKO mice compared with DKO mice. Striking differences were also visible in the blood and thymus and spleen with two- to three-fold increased cell numbers after 3 months in SIRP-DKO mice compared with DKO mice. Interestingly, the overall composition of the hematopoietic system in the spleen was similar in DKO, hSIRPα-DKO, and NOD-based mice, indicating that hSIRPα expression affects the efficiency of initially transferred stem and progenitor cells to seed the bone marrow and subsequently differentiate into various lineages of cells. However, some significant differences were observed, which include increased frequencies of CD3-NKp46+ cells in the spleen and significantly increased numbers of CD4+CD8+ double-positive thymocytes. Not to be bound by any theory, the latter might be a direct result of decreased phagocytic activity in this organ, which contains numerous phagocytes normally responsible for removing negatively selected thymocytes. Alternatively, this might also be a consequence of increased CD47 signaling in developing T cells as ligation of CD47 sends costimulatory signals (1997, Reinhold et al., J Exp Med 185:1-11; 1997, Ticchioni et al., J Immunol 158:677-684; 2001, Latour et al., J Immunol 167:2547-2554). Another notable difference was observed when mice were analyzed for the presence of platelets and erythrocytes. Whereas hSIRPα-DKO mice had an increased number of human platelets compared with DKO mice, they did not reach levels observed in NSG mice. Similarly, frequencies of erythrocytes were significantly higher in NSG mice compared with DKO and hSIRPα-DKO mice. Not to be bound by any particular theory, this might be the result of additional strain-specific mutations beyond SIRPα that either favor development or persistence of these cell lineages in vivo (1995, Shultz et al., J Immunol 154:180-191). Longitudinal analysis of engraftment in DKO and hSIRPα-DKO mice revealed that, whereas DKO mostly lost human cells after 9 month, they were still routinely detectable in hSIRPα-DKO mice. This could be mediated either by prolonged hematopoiesis in the bone marrow or enhanced survival of differentiated cells in the peripheral organs of hSRIPα-transgenic mice.

Furthermore, more +huSIRPα mice produced antigen-specific IgG. To provide help for B cells, antigen-specific T cells need to recognize antigens presented in the context of MHC molecules. Hence, although not wishing to be bound by any particular theory, the increased functionality in SIRP-DKO mice may be the result of improved selection and differentiation of T cells in vivo due to overall higher numbers of human immune cells. Similarly, HLADR4 transgenic mice and humanized mice that are generated by cotransplantation of CD34+ cells and human fetal thymus pieces have improved HLA-restricted T cell responses and also improved antigen-specific antibody responses (2011, Danner et al., PLoS ONE 6:e19826; 2009, Brainard et al., J Virol 83:7305-7321).

With the hSIRPα-DKO mice, a strain has been generated that combines superior engraftment level and the possibility of long-term genetic manipulations to further enhance the murine host. In hSIRPα-DKO mice, immunization with a T cell-dependent antigen induced stronger immune responses as measured by higher titers of antigen-specific IgM compared with DKO mice.

In summary, the results disclosed herein demonstrate improved frequencies of engrafted mice and increased levels of engraftment of human cells by transgenic expression of hSIRPα in 129/BALB/c Rag2$^{-/-}$γc$^{-/-}$ mice, resulting in an improved functionality of the human immune system in vivo. Genetic engineering in the mouse strains described herein can be used to rapidly generate mice expressing genes of interest and analyze their influence on engraftment of human tissues and cells. On the basis of the successful completion of diverse genetic modifications such as the replacement of complete mouse genes with their human counterparts and expression of human genes using BAC transgenes, this approach enables targeted modifications to further improve the murine host for transplantation of human tissues and cells.

Example 1 hSIRPα is Faithfully Expressed and Functional in hSIRPα-Transgenic Mice

Figure 5:
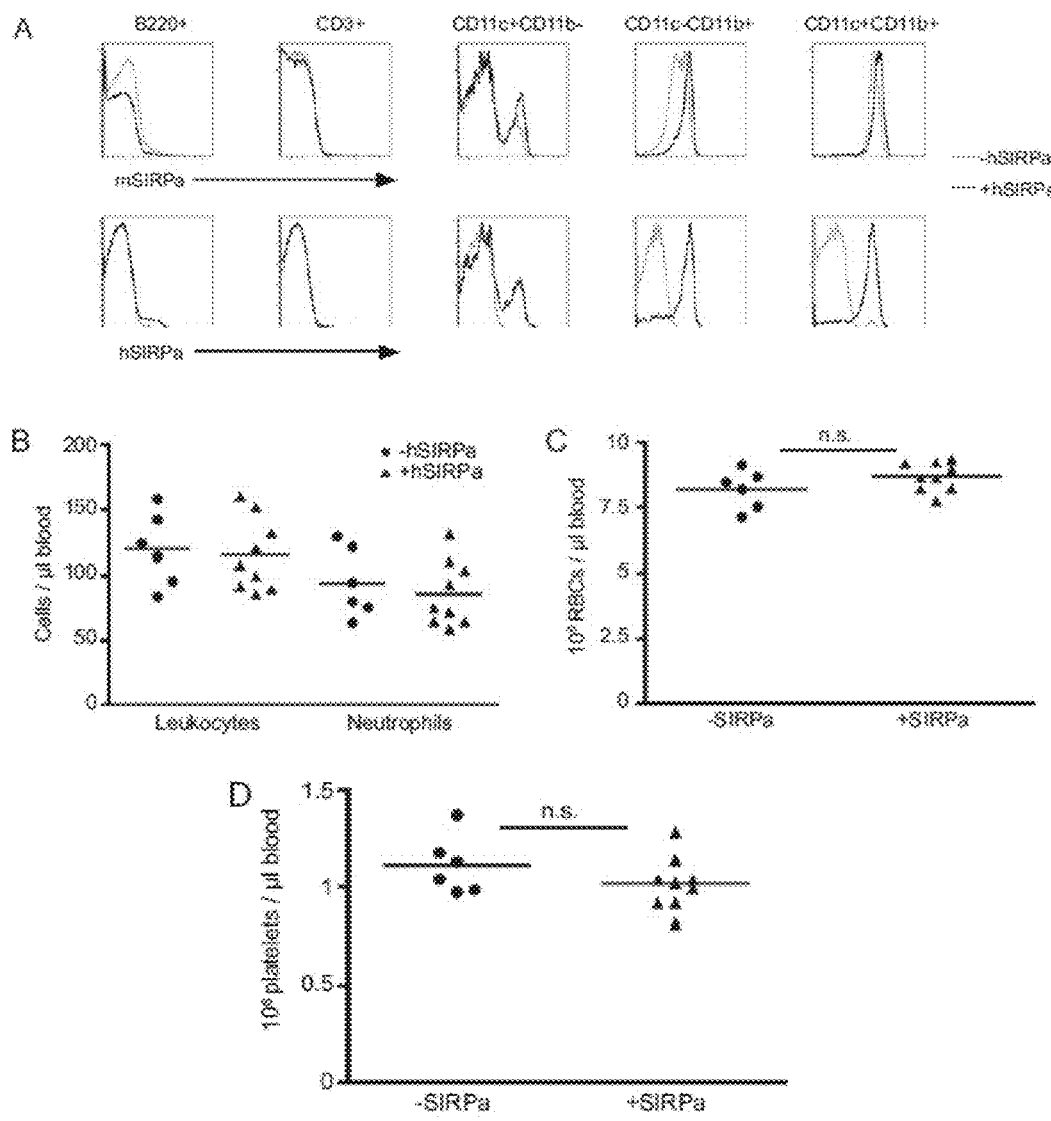
FIG. 5, comprising
Figure 6:
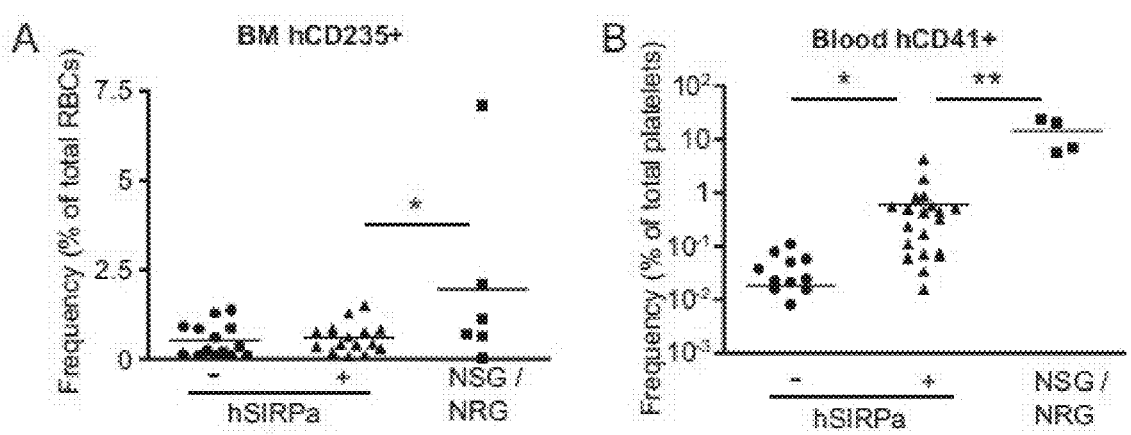
FIG. 6 depicts the results of experiment assessing the frequency of $hCD235^+$ red blood cells in the bone marrow, 12-14 weeks post transplantation, and $hCD41^+$ platelets in the blood 10-12 weeks post transplantation, in different mouse strains.

A bacterial artificial chromosome encompassing the coding region of huSIRPα was identified and engineered to contain a eukaryotic selection marker to allow transgenesis in ES cells. hSIRPα-transgenic Rag2$^{-/-}$γc$^{-/-}$ (hSIRPα-DKO) mice expressing the human transgene under the human regulatory elements were generated after targeting an ES cell line ($F_1$ 129/BALB/c Rag2$^{+/-}\gamma c^{y/-}$), which can easily be genetically manipulated (2011, Rongvaux et al., Proc Natl Acad Sci USA 95:5320-25; 2011, Proc Natl Acad Sci USA 108:2390-95). Upon obtaining several lines of hSIRPα-expressing mice, the expression levels of hSIRPα were analyzed on mouse CD45$^+$ cells by flow cytometry. hSIRPα was faithfully expressed in BAC-transgenic mice as cells expressing mouse SIRPα expressed also hSIRPα (FIG. 1A and FIG. 5A). In contrast, no hSIRPα expression was detected on cells not expressing mouse SIRPα. hSIRPα-DKO mice had similar numbers of leukocytes, including neutrophils and monocytes, in the blood and did not show any signs of thrombocytopenia and anemia, which is a prominent feature in SIRPα$^{-/-}$ mice (2002, Yamao et al., J Biol Chem 277: 39833-39) (FIG. 5B-D). This indicates that expression of hSIRPα does not interfere with the function of mSIRPα in vivo. Clearance of erythrocytes is regulated in vivo in a CD47-SIRPα-dependent manner (2000, Oldenborg et al., Science 288:2051-54). To evaluate if hSIRPα was functional on mouse cells, human erythrocytes that express CD47 were injected into BALB/c Rag2$^{-/-}\gamma c^{-/-}$ (DKO), hSIRPα-DKO, and NOD/scid/y$_c^{-/-}$ (NSG) mice and their clearance was monitored. Similarly to NSG mice, significantly higher numbers of erythrocytes were present in the blood of hSIRPα-DKO mice compared with DKO mice, indicating that hSIRPα is functional in the mouse in vivo, negatively regulating phagocytosis and thus elimination of human CD47-expressing cells (FIGS. 1B and C).

Example 2

Multilineage Engraftment in the Blood of hSIRPα-DKO Mice

To test whether hSIRPα expression in immunocompromised mice would lead to increased engraftment levels after human CD34$^+$ cell transplantation, human fetal liver-derived CD34+ cells, a population highly enriched in HSPCs, were transplanted into newborn irradiated DKO, hSIRPα-DKO, and NSG mice. A total of 88% of engrafted hSIRPα-DKO mice had greater than 1% human CD45$^+$ cells in the peripheral blood, which is similar to NSG mice, whereas only 52% of DKO surpassed this value (Table 1).

TABLE 1

Engraftment of different strains of immunodeficient mice

| | Engraftment | | |
|---|---|---|---|
| | Engrafted at birth | Alive after 3 mo | >1% engrafted (%) |
| DKO | 165 | 135 | 70 (52) |
| hSIRP | 155 | 124 | 109 (88) |
| NSG | 75 | 51 | 41 (80) |
| I test$^\dagger$ | — | 0.0455* | <0.0001$^\dagger$ |

*Tests difference of fraction of mice alive after 3 mo from total number of engrafted mice between the strains.
$^\dagger$Tests difference of fraction of mice with engraftment levels higher than 1% from mice alive after 3 mo between the strains.

Compared with DKO mice, NSG mice had significantly higher frequencies of human CD45$^+$ cells in the blood of engrafted mice, 10-12 wk after transplantation (6.6% compared with 17.6%, P<0.001) (FIG. 2B). Strikingly, hSIRPα-DKO had increased frequencies of human CD45$^+$ cells compared with DKO mice (23.3% compared with 6.6%, P<0.001) reaching levels at least similar to NSG mice (FIG. 2B). DKO and hSIRPα-DKO mice were further compared to NOD/Rag1/γc$^{-/-}$ (NRG) mice (2008, Pearson T, et al., Clin Exp Immunol 154: 270-84). NRG mice had significantly higher engraftment levels compared with DKO (29.6% compared with 6.6%, P<0.001), and similar high engraftment levels as NSG and hSIRPα-DKO. Hence, no significant differences were found between hSIRPα-DKO mice and NOD-based strains. As previously described, in vivo multilineage development of human CD45$^+$ cells was able to be detected in all models (FIG. 2C-E and FIG. 6). When these mice were analyzed in detail, the overall composition of human CD45$^+$ cells regarding B cells and myeloid cells was similar in all mouse strains (FIG. 2C-E). Notably, an increase in T cell frequency in the blood of hSIRPα-DKO mice compared with DKO and NSG mice was detected, which was not seen when hSIRPα-DKO mice were compared with NRG mice (hSIRPα, 40% compared with DKO, 29.3%; NSG, 19.6%; and NRG, 45%, respectively).

Example 3

Reduced Mortality of hSIRPα-DKO Mice

In comparison with NSG mice, hSIRPα-DKO mice were equally well engrafted, but a slightly increased early mortality (<12 wk) of engrafted NSG mice was observed, which can likely be attributed to increased gamma-irradiation sensitivity of scid strains compared with Rag1/Rag2-deficient strains (Table 1). As a consequence, fewer engrafted mice can be used for experiments (DKO, 40%; hSIRPα-DKO, 70%; and NSG, 53%) (Table 1). It is noted that the difference in survival became larger at later time points (Table 2). In line with a previous report, no NSG mice were alive after 9 mo, impairing the value of this model for long-term studies (2007, Wanatabe et al., J Virol 81:13259-64).

TABLE 2

Survival of different strains of immunodeficient mice

| | Survival | | |
|---|---|---|---|
| | Start at 3 mo | Alive after 6 mo | Alive after 9 mo |
| DKO | 15 | 14 | 12 |
| SIRP | 18 | 16 | 13 |
| NSG | 12 | 11 | 0 |
| I test$^\dagger$ | — | 0.9952* | >0.0001* |

*Tests difference of fraction of mice alive at indicated time point from mice assigned to the group after 3 mo between the strains.

Example 4

Enhanced Human Cell Engraftment in the Bone Marrow and the Periphery of hSIRPα Mice Bone marrow, spleen, and thymus were analyzed 12-14 wk posttransplantation to characterize whether similar differences could be found in these hematopoietic organs. In the bone marrow, hSIRPα-DKO and NSG and NRG mice (which were analyzed together in the subsequent experiments) contained significantly higher frequencies and total numbers of hCD45$^+$ cells than DKO mice (FIGS. 2G and H). As observed in blood, the composition of hCD45$^+$ in the bone marrow was not different between the different strains with similar frequencies of CD34$^+$ HSPCs, CD19$^+$ B cells, CD33$^+$SSC$^{low}$ monocytes/dendritic cells, and CD33$^{int}$CD66$^+$SSC$^{high}$ granulocytes. Nevertheless, due to increased total numbers of hCD45$^+$ cells, the numbers of all subsets including CD34$^+$ and CD34+CD38− cells, a population enriched for human early progenitor cells and HSPCs, were significantly increased in hSIRPα-DKO mice (FIGS. 2I and J). Further analysis showed that also frequencies of human CD45+ cells in the spleen were increased in SIRP-DKO mice, reaching levels observed in NSG and NRG mice (FIGS. 3A and B). Besides an increase in the frequency of CD3−NKp46+ cells, which include predominantly NK cells but also lymphoid tissue inducer cells, in hSIRPα-DKO mice (2.8% vs. 1.3%, P<0.03), overall composition was not significantly different between DKO and hSIRPα-DKO mice (FIGS. 3D and E and FIG. 7). Notably, in contrast to the peripheral blood NSG/NRG mice had slightly higher CD3+ T cell numbers, but lower CD19+ B cell numbers compared with hSIRPα-DKO mice, whereas overall hCD45+ numbers were similar. In all groups of mice, the ratio between CD4+ and CD8+ T cells was similar to the ratio found in humans (FIG. 7). In all mouse strains, CD4− T cells consisted of naïve cells (CCR7+ CD45RO−) and subsets of memory cells (CCR7+/− CD45RO+) with a significant variability between mice (FIG. 7). In the thymus, hSIRPα-DKO mice had higher numbers of total hCD45+ cells and CD4+CD8+ thymocytes compared with the DKO mice (FIGS. 3G and H). Cell numbers were also higher than observed in NSG mice, indicating that additional strain-specific factors or even better interaction of human CD47 and huSIRPα compared with human CD47 and NOD-SIRPα might influence T cell development and maintenance in this inbred strain.

Example 5

Enhanced Human Cell Maintenance in hSIRPα Mice

The duration of human hematopoiesis after engraftment of human stem and progenitor cells is limited as demonstrated by relatively low recovery of cells that are able to efficiently engraft secondary recipients in vivo (2011, Rongvaux et al., Proc Natl Acad Sci USA 94: 5320-25; 1997, Hogan et al, Blood 90: 85-96). Accordingly, steady decrease of human cell numbers in the bone marrow was observed. At 23-26 wk, numbers of hCD45+ were around one-third of the numbers after 12-14 wk in DKO and hSIRPα-DKO mice and NSG/NRG mice (FIGS. 8A and B). Cell numbers further decreased with time and hCD45+ cells could be recovered in significant numbers only from hSIRPα-DKO after 35-37 wk (FIGS. 8A and B). NSG mice were unable to be analyzed at this late time point, because of a high mortality that became apparent beyond 6 mo (Table 2), which has also been reported previously (2007, Wanatabe et al., J Virol 81: 13258-64). In the spleen, a similar trend was observed, with cell numbers declining in all strains of mice from 3 to 6 months (FIGS. 8C and D). Notably, in hSIRPα-DKO, numbers in the spleen did not decline much further between 6 and 9 months, indicating that differentiated cells can persist in these mice (FIGS. 8C and D). At 24 and 36 wk postengraftment, hSIRPα-DKO mice contained on average 3.3-fold and 5.1-fold more human CD45+ cells in the spleen than DKO mice, respectively. At later time points, the frequency of T cells increased, whereas the frequency of B cells decreased (FIG. 8E-H). In summary, these results indicate that hSIRPα-DKO mice lose the ability for human hematopoiesis in a similar way to DKO mice, likely due to the loss of HSPCs; however, they have a superior capacity to maintain differentiated cells in the periphery.

Example 6

Increased Antigen-Specific Humoral Immune Responses in hSIRPα-Transgenic Mice

Figure 4:
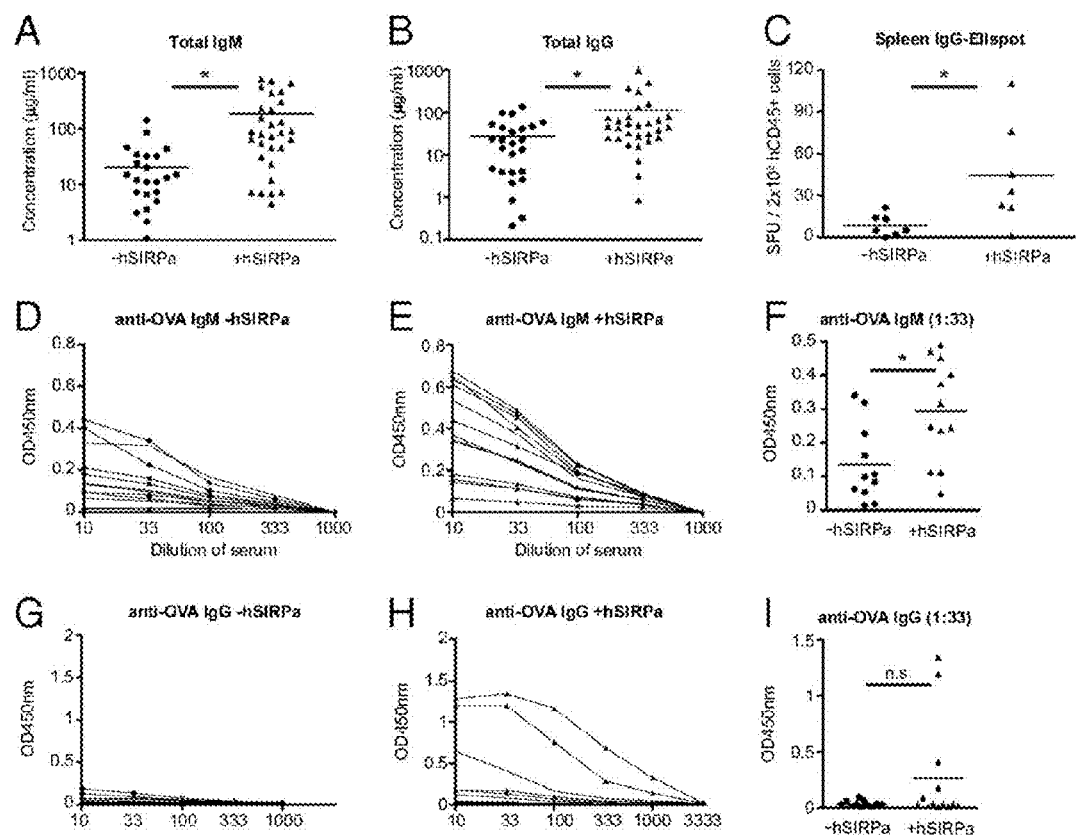
FIG. 4, comprising

To test whether the increase of human immune cells translated into quantitative and qualitative changes of the human adaptive immune system in vivo, total levels of human immunoglobulins in mice 12-16 wk postengraftment were analzyed. Indeed, compared with DKO mice, hSIRPα-DKO mice had increased levels of human IgM (185±55 µg/mL vs. 24±9 µg/mL, P<0.03, mean±SEM) and IgG (113±36 µg/mL vs. 26±6 µg/mL, P<0.02) in the plasma (FIGS. 4A and B). Accordingly, a higher number of human IgG-producing cells were detected in the spleen of hSIRPα-DKO mice (FIG. 4C). This correlated with an increased frequency of CD27+ memory B cells in the spleen (FIG. 9). Next, DKO and hSIRPα-DKO mice were immunized with a protein antigen (ovalbumin, OVA) mixed with an adjuvant (complete Freund's adjuvant) to assess the de novo development of antigen-specific immune responses. Because most studies using CD34+ cell-engrafted mice reported only low levels of antigen-specific immune responses, this potent adjuvant was used to provide the strongest conditions for priming of de novo immune responses (2002, Ito et al., Blood 100:3175-82; 2005, Ishikawa et al., Blood 106:1565-73; 2006, Baenziger et al., Pro Natl Acad Sci USA 103:15951-56). Mice were boosted 2 wk later with OVA/incomplete Freund's adjuvant and bled 10 d after the boost. Whereas nonimmunized DKO and hSIRPα-DKO did not have significant levels of anti-OVA antibodies (IgM, IgG), anti-OVA IgM was detected in 66.6% (12 of 18) of DKO mice and in 88% (21 of 24) of hSIRPα-DKO mice (Table 3).

TABLE 3

Antigen-specific immune responses after immunization

| Number of mice | DKO | SRP |
|---|---|---|
| Vaccinated | 18 | 24 |
| Responded (IgM) | 12 | 21 |
| % responded (IgM) | 66.7 | 87.5 |
| Fisher's exact test (IgM) | | P = 0.1391 |
| Responded (IgG) | 2 | 16 |
| % responded (IgG) | 11.1 | 66.7 |
| Fisher's exact test (IgG) | | P = 0.0032 |

Using endpoint dilution of the sera of immunized mice, antibody titers were determined for IgM and IgG from individual mice. For anti-OVA IgM, there was no significant difference in the frequency of mice responding between the two groups, nevertheless hSIRPα-DKO mice had increased antibody titers compared with DKO mice (FIG. 4D-F). When antigen-specific IgG were analyzed, a more striking difference was discernible. In only 2 out of 18 (11%) DKO mice could antigen-specific IgG be detected, whereas IgG was detectable in 16 of 24 (66.6%) hSIRPα-DKO mice (Table 3 and FIG. 4G-I). In summary, upon immunization significant difference in the levels of specific antibody responses was observed, as evidenced by the higher IgM titers in hSIRPα-DKO mice and a higher frequency of hSIRPα-DKO mice producing antigen-specific IgG. This will have important implications for the further development of this platform for human vaccine development.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A transgenic immunodeficient mouse having a genome comprising a nucleic acid encoding human signal regulatory protein alpha (SIRPα) operably linked to a human SIRPα promoter, wherein the mouse expresses the human SIRPα.

2. The transgenic immunodeficient mouse of claim 1 wherein the mouse does not express recombination activating gene 2 (Rag-2$^{-/-}$).

3. The transgenic immunodeficient mouse of claim 1 wherein the mouse does not express IL2 receptor gamma chain (gamma chain$^{-/-}$).

4. The transgenic immunodeficient of claim 1 wherein the mouse does not express Rag-2 or IL2 receptor gamma chain (Rag-2$^{-/-}$ gamma chain$^{-/-}$).

5. The transgenic mouse of claim 1, further comprising human hematopoietic stem and progenitor cells (HSPCs).

6. The transgenic mouse of claim 1, further comprising the progeny of HSPCs.

7. A method of engraftment of a human hematopoietic stem and progenitor cells (HSPC) into a transgenic immunodeficient mouse comprising: engrafting a human HSPC into the transgenic immunodeficient mouse of claim 1.

8. The method of claim 7, wherein the transgenic immunodeficient mouse does not express recombination activating gene 2 (Rag-2$^{-/-}$).

9. The method of claim 7, wherein the transgenic immunodeficient mouse does not express endogenous IL2 receptor (gamma chain$^{-/-}$).

10. The method of claim 7, wherein the transgenic immunodeficient mouse does not express endogenous Rag-2 or gamma chain (Rag-2$^{-/-}$ gamma chain$^{-/-}$).

* * * * *